(12) United States Patent
Karlish et al.

(10) Patent No.: US 9,938,316 B2
(45) Date of Patent: Apr. 10, 2018

(54) SELECTIVE INHIBITORS OF α2 ISOFORM OF NA,K-ATPASE AND USE THEREOF FOR REDUCTION OF INTRA-OCULAR PRESSURE AND AS CARDIOTONIC AGENTS

(71) Applicant: Yeda Research and Development Co. Ltd., Rehovot (IL)

(72) Inventors: Steven J. D. Karlish, Rehovot (IL); Adriana Katz, Rehovot (IL); Daniel M. Tal, Rehovot (IL); Arie Marcovich, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 14/913,366

(22) PCT Filed: Aug. 27, 2014

(86) PCT No.: PCT/IL2014/050773
§ 371 (c)(1),
(2) Date: Feb. 21, 2016

(87) PCT Pub. No.: WO2015/029035
PCT Pub. Date: Mar. 5, 2015

(65) Prior Publication Data
US 2016/0244479 A1 Aug. 25, 2016

Related U.S. Application Data

(60) Provisional application No. 61/871,328, filed on Aug. 29, 2013.

(51) Int. Cl.
*C07J 43/00* (2006.01)
*C07J 19/00* (2006.01)

(52) U.S. Cl.
CPC ............ *C07J 43/003* (2013.01); *C07J 19/005* (2013.01)

(58) Field of Classification Search
CPC ............................. C07J 43/003; C07J 19/005
See application file for complete search history.

(56) References Cited

U.S. PATENT DOCUMENTS

| | | | |
|---|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling et al. |
| 3,879,262 A | 4/1975 | Schuurs et al. |
| 3,901,654 A | 8/1975 | Gross |
| 3,935,074 A | 1/1976 | Rubinstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,190,496 A | 2/1980 | Rubinstein et al. |
| 4,666,828 A | 5/1987 | Gusella |
| 4,683,202 A | 7/1987 | Mullis |
| 4,801,531 A | 1/1989 | Frossard |
| 4,879,219 A | 11/1989 | Wands et al. |
| 5,011,771 A | 4/1991 | Bellet et al. |
| 5,192,659 A | 3/1993 | Simons |
| 5,272,057 A | 12/1993 | Smulson et al. |
| 5,281,521 A | 1/1994 | Trojanowski et al. |
| 5,972,630 A | 10/1999 | Cromer et al. |
| 2003/0207431 A1 | 11/2003 | Ghoshal et al. |
| 2004/0210044 A1 | 10/2004 | Slattum et al. |
| 2008/0199895 A1 | 8/2008 | Karlish et al. |

FOREIGN PATENT DOCUMENTS

| | | |
|---|---|---|
| DE | e 224037 | 6/1985 |
| EP | 0532187 | 3/1993 |
| FR | 2262670 | 9/1975 |
| WO | WO 98/52961 | 11/1998 |
| WO | WO 2006/044916 | 4/2006 |
| WO | WO 2007/016656 | 2/2007 |
| WO | WO 2015/029035 | 3/2015 |
| WO | WO 2017/013637 | 1/2017 |
| WO | WO 2017/013648 | 1/2017 |

OTHER PUBLICATIONS

Serrano-Wu et al., Bioorg. Med. Chem. Lett., 2002, 12, p. 2757-2769.*
Communication Relating to the Results of the Partial International Search dated Oct. 17, 2016 From the International Searching Authority Re. Application No. PCT/IL2016/050785.
Office Action and Search Report dated Oct. 17, 2016 From the State Intellectual Property Office of the People's Republic of China. Re. Application No. 201480059614.5 and its Translation Into English.
International Search Report and Written Opinion dated Dec. 19, 2016 From the International Searching Authority Re. Application No. PCT/IL2016/050785. (23 Pages).
Office Action dated May 2, 2017 From the State Intellectual Property Office of the People's Republic of China Re. Application No. 201480059614.5 and Its Translation Into English. (10 Pages).
Communication Relating to the Results of the Partial International Search dated Oct. 27, 2015 From the International Searching Authority Re. Application No. PCT/IL2015/050741.
International Preliminary Report on Patentability dated Mar. 10, 2016 From the International Bureau of WIPO Re. Application No. PCT/IL2014/050773.
International Search Report and the Written Opinion dated Nov. 18, 2014 From the International Searching Authority Re. Application No. PCT/IL2014/050773.
International Search Report and the Written Opinion dated Jan. 22, 2016 From the International Searching Authority Re. Application No. PCT/IL2015/050741.
Official Action dated Dec. 1, 2009 From the U.S. Patent and Trademark Office Re. U.S. Appl. No. 11/905,833.
Official Action dated Apr. 2, 2010 From the U.S. Patent and Trademark Office Re. U.S. Appl. No. 11/905,833.

(Continued)

*Primary Examiner* — Jonathan S Lau

(57) ABSTRACT

The present invention relates to digoxin and digitoxin derivatives that are selective inhibitors of the α2 isoform of Na,K-ATPase, and that reduce intra-ocular pressure. The invention further relates to uses of these derivatives for treating disorders associated with elevated intraocular pressure, such as glaucomas, and/or as cardiotonic agents.

10 Claims, 22 Drawing Sheets

(56) References Cited

OTHER PUBLICATIONS

Adamczyk et al. "Digoxin Dialdehyde Reductive Aminations. Structure Proof of the Perhydro-1,4-Oxazepine Product", Steroids, XP004026467, 60(11): 753-758, Nov. 1, 1995. Compound 3, Preparation Thereof in Scheme 1, p. 754, col. 1.

Adamczyk et al. "Unexpectedly Facile Hydrolysis of Digoxin Esters. The Importance of Appropriate Controls in Lipase-Mediated Hydrolysis", The Journa of Organic Chemistry, XP055221120, 60(11): 3557-3560, Jun. 1, 1995. Table 1, Compounds 7a-7e, Preparation Thereof on p. 3559, col. 1.

Bers "Cardiac Excitation-Contraction Coupling", Nature, 415: 198-205, Jan. 10, 2002.

Bitter "Heterologous Gene Expression in Yeast", Methods in Enzymology, 152(Chap.70): 673-684, 1987.

Bitter et al. "Expression and Secretion Vectors for Yeast", Methods in Enzymology, 153(Chap.33): 516-544, 1987.

Cohen et al. "Purification of Na+,K+-ATPase Expressed in Pichia Pastoris Reveals an Essential Role of Phospholipid-Protein Interactions", The Journal of Biological Chemistry, 280(17); 16610-16618, Apr. 29, 2005.

Cornelius "Cholesterol Modulation of Molecular Activity of Reconstituted Shark Na+,K+-ATPase", Biochimica et Biophysica Acta, 1235: 205-212, 1995.

Cornelius "Modulation of Na,K-ATPase and Na-ATPase Activity by Phospholipids and Cholesterol. I. Steady-State Kinetics", Biochemistry, 40(30); 8842-8851, 2001.

Crambert et al. "New Molecular Determinants Controlling the Accessibility of Quabain to Its Binding Site in Human Na,K-ATPase α Isoforms", Molecular Pharmacology, 65(2): 335-341, 2004.

Crambert et al. "Transport and Pharmacological Properties of Nine Different Human Na,K-ATPase Isozymes", The Journal of Biological Chemistry, 275(3): 1976-1986, Jan. 21, 2000.

Ferrari et al. "PST2238: A New Antihypertensive Compound That Antagonizes the Long-Term Pressor Effect of Ouabain", The Journal of Pharmacology and Experimental Therapeutics, JPET, 285(1): 83-94, 1998.

Ferrari et al. "Rostafuroxin: An Ouabain Antagonist That Corrects Renal and Vascular Na+-K+-ATPase Alterations in Ouabain and Adducin-Dependent Hypertension", American Journal of Physiology—Regulatory, Integrative and Comparative Physiology, 290: R529-R535, 2006.

Hardt et al. "Effect of Systemic Digitalis Application on Intraocular Pressure [Zum Einfluss von Systemischer Digitalis-Applikation auf den Intraocularen Druck]", Graefe's Archive for Clinical and Experimental Ophthalmology, 219(2): 76-79, Aug. 1982. Abstract.

Hartmanis et al. "Solubilization of a Membrane-Bound Diol Dehydratase With Retention of EPR G=2.02 Signal by Using 2-(N-Cyclohexylamino)Ethanesulfonic Acid Buffer", Proc. Natl. Acad. Sci. USA, 84: 76-79, Jan. 1987.

Haviv et al. "Stabilization of Na+,K+-ATPase Purified From Pichia Pastoris Membranes by Specific Interactions With Lipids", Biochemistry, 46: 12855-12867, Published on Web Oct. 16, 2007.

Hayashi et al. "Minimum Enzyme Unit for Na+/K+-ATPase Is the αβ-Promoter. Determination by Low-Angle Laser Light Scattering Photometry Coupled With High-Performance Gel Chromatography for Substantially Simultaneous Measurement of ATPase Activity and Molecular Weight", Biochimica et Biophysica Acta, 983: 217-229, 1989.

Jørgensen "Purification of Na+,K+-ATPase: Enzyme Sources, Preparative Problems, and Preparation From Mammalian Kidney", Methods in Enzymology, 156(2): 29-43, 1988.

Jørgensen et al. "Role of Conserved TGDGVND-Loop in Mg2+Binding, Phosphorylation, and Energy Transfer in Na,K-ATPase", Journal of Bioenergetics and Biomembranes, 35(5): 367-377, Oct. 2001.

Juhaszova et al. "Distinct Distribution of Different Na+ Pump α Subunit Isoforms in Plasmalemma", Annals New York Academy of Sciences, 834: 524-536, 1997.

Kapri-Pardes et al. "Stabilization of the Alpha2 Isoform of Na,K-ATPase by Mutations in a Phospholipid Binding Pocket", The Journal of Biological Chemistry, 286(50): 42888-42899, Dec. 16, 2011.

Katz et al. "Digoxin Derivatives With Enhanced Selectivity for the Alpha2 Isoform of Na,K-ATPase. Effects on Intraocular Pressure in Rabbits", The Journal of Biological Chemistry, 289(30): 21153-21162, Jul. 25, 2014.

Katz et al. "Selectivity of Digitalis Glycosides for Isoforms of Human Na,K- ATPase", The Journal of Biological Chemistry, 285(25): 19582-19592, JBC Papers in Press Apr. 13, 2010.

Keating et al. "Potentiometric Digoxin Antibody Measurements With Antigen-Ionophore Based Membrane Electrodes", Analytical Chemistry, XP055221088, 56(4): 801-806, Apr. 1984. Fig.2, Final Compound, Compounds Analyzed in Figs.3-4, Preparation.

Laursen et al. "Structures and Characterization of Digoxin- and Bufalin-Bound Na+, K+-ATPase Compared With the Ouabain-Bound Complex", Proc. Natl. Acad. Sci. USA, PNAS, 112(6): 1755-1760, Feb. 10, 2015.

Lifshitz et al. "Functional Interactions of Phospholemman (PLM) (FXYD1) With Na+,K+-ATPase. Purification of α1/β1/PLM Complexes Expressed in Pichia Pastoris", The Journal of Biological Chemistry, 281(23): 15790-15799, Jun. 9, 2006.

Lifshitz et al. "Purification of the Human Alpha2 Isoform of Na,K-ATPase Expressed in Pichia Pastoris. Stabilization by Lipids and FXYD1", Biochemistry, 46: 14937-14950, Published on Web Dec. 2, 2007.

Lingrel "Na,K-ATPase: Isoform Structure, Function, and Expression", Journal of Bioenergetics and Biomembrane, 24(3): 263-270, 1992.

Mishra et al. "FXYD Proteins Stabilize Na,K-ATPase. Amplificaiton of Specific Phosphatidylserine-Protein Interactions", The Journal of Biological Chemistry, 286(11): 9699-9712, Mar. 18, 2011.

Müller-Ehmsen et al. "Ouabain and Substrate Affinities of Human Na+ -K+ - ATPase α3β1, α2β1 and α3β1 When Expressed Separately in Yeast Cells", American Journal of Physiology—Cell Physiology, 281: C1355-C1364, Oct. 2001.

Roeder et al. "Radioiodination of Hydroxyphenyl-Ethylamine Derivatives of Some Digitalisglycosides and Their Aglycones [Zur Radiojodmarkierung von Tyraminderivativen Einiger Digitalisglykoside and Deren Aglyka]", Journal of Labelled Compounds and Radiopharmaceuticals, XP055221078, 15: 197-214, Jan. 1978. Compounds 19, 20, 25, 26, Preparation.

Specht et al. "Two Different Na,K-ATPases in the Optic Nerve: Cells of Origin and Axonal Transport", Proc. Natl. Acad. Sci. USA, 81: 1234-1238, Feb. 1984.

Strugatsky et al. "Expression of Na+,K+-ATPase in Pichia Pastoris. Analysis of Wild Type and D369N Mutant Proteins by Fe2+-Catalyzed Oxidative Cleavage", The Journal of Biological Chemistry, 278(46): 46064-46073, Nov. 14, 2003.

Sweadner "Isozymes of the Na+/K+-ATPase", Biochimica et Biophysica Acta, 988: 185-220, 1989.

Sweadner "Two Molecular Froms of (Na+ + K+)-Stimulated ATPase in Brain. Separation, and Difference in Affinity for Strophanthidin", The Journal of Biological Chemistry, 254(13): 6060-6067, Jul. 10, 1979.

Tian et al. "Signal-Transducing Function of Na+-K+-ATPase Is Essential for Ouabain's Effect on [Ca2+]I in Rat Cardiac Myocytes", American Journal of Physiology—Heart and Circulation Physiology, 281: H1899-H1907, 2001.

Xie et al. "Na+/K+-ATPase as a Signal Transducer", European Journal of Biochemistry, 269: 2434-2439, Feb. 2002.

Yeagle et al. "Effects of Cholesterol on (Na+,K+)-ATPase ATP Hydrolyzing Activity in Bovine Kidney", Biochemistry, 27: 6449-6452, 1988.

Supplementary European Search Report and the European Search Opinion dated Mar. 3, 2017 From the European Patent Office Re. Application No. 14839412.5. (10 Pages).

(56) References Cited

OTHER PUBLICATIONS

Bachrach et al. "Attachment of Drugs to Polydimethylsiloxanes", European Polymer Journal, XP024053540, 20(5): 493-500, Jan. 1984. Abstract, p. 498, col. 1, Para 1-2, Compound I.

Ferraiolo et al. "Digoxin-Induced Decrease in Intraocular Pressure in the Cat", European Journal of Pharmacology, XP023839155, 55(1): 19-22, Apr. 1, 1979. Abstract.

Ham et al. "Heart Uptake of Radioiodine Labeled Cardenolides", Journal of Labelled Compounds and Radiopharmaceuticals, XP055348816, 13(2): 222-223, Jan. 1977. p. 222, Para 3-5, p. 223, Compound I.

International Preliminary Report on Patentability dated Feb. 1, 2018 From the International Bureau of WIPO Re. Application No. PCT/IL2015/050741. (16 Pages).

International Preliminary Report on Patentability dated Feb. 1, 2018 From the International Bureau of WIPO Re. Application No. PCT/IL2016/050785. (15 Pages).

* cited by examiner

METHODS:
- New Zealand white Rabbits
- Acute IOP elevation:
  - 4AP (40 mg/ml, 30 µl)
  - IB-MECA (1 µM, 30 µl)
- IOP measurement
  - using Pneumatonometer

SELECTIVE INHIBITORS OF α2 ISOFORM OF NA,K-ATPASE AND USE THEREOF FOR REDUCTION OF INTRA-OCULAR PRESSURE AND AS CARDIOTONIC AGENTS

RELATED APPLICATIONS

This application is a National Phase of PCT Patent Application No. PCT/IL2014/050773 having International filing date of Aug. 27, 2014, which claims the benefit of priority under 35 USC § 119(e) of U.S. Provisional Patent Application No. 61/871,328 filed on Aug. 29, 2013. The contents of the above applications are all incorporated by reference as if fully set forth herein in their entirety.

FIELD OF THE INVENTION

The present invention relates to digoxin and digitoxin derivatives that are selective inhibitors of the α2 isoform of Na,K-ATPase, and that reduce intra-ocular pressure. The invention further relates to uses of these derivatives for treating disorders associated with elevated intraocular pressure, such as glaucomas, and/or as cardiotonic agents.

BACKGROUND OF THE INVENTION

Glaucoma is a disease leading to irreversible blindness. Control of intra-ocular pressure (IOP) is the mainstay of current therapy of glaucoma, and is achieved by various drugs, such as β-blockers, prostaglandin analogues, α2 adrenergic receptor agonists, cholinergic agonists and carbonic anhydrase inhibitors given topically or systemically. The topical route is preferable, provided the drug effectively permeates the cornea, because this minimizes systemic side-effects. Despite the selection of drugs available, uncontrolled IOP in many patients eventually makes surgical intervention necessary. Thus, fresh approaches to drug treatment of glaucoma are highly desirable.

The Na,K-ATPase is the motor for production of the aqueous humour in the ciliary body epithelium and, in principle, inhibition of the Na,K-ATPase should suppress the production of aqueous humour, and control IOP. Control of IOP is the mainstay of glaucoma therapy, but despite the selection of drugs available, fresh approaches to drug treatments are highly desirable. Previously, intra-venous digoxin, a classical inhibitor of the Na,K-pump, used primarily to treat congestive heart failure, was considered for this role but was discarded due to systemic toxicity (1,2).

The Na,K-ATPase consists of α and β subunits (αβ) and accessory FXYD regulatory subunits. There are four isoforms of the α1 subunit (α1-4) and three isoforms of the β subunit (β1-3) expressed in a tissue-specific fashion, α1 is the common isoform that maintains Na and K gradients in all tissues, while α2 is expressed mainly in muscle and astrocytes, and α3 in nerve cells. Human heart expresses α1 (c.70%) and both α2 and α3 isoforms (c.30%) and β1. The ciliary epithelium in the eye is a functional syncytium consisting of apical pigmented cells (PE) oriented towards the blood and baso-lateral non-pigmented (NPE) cells oriented towards the anterior chamber of the eye.

It is known that the primary Na,K-ATPase isoform of the PE is α1β1 while that of the NPE is α2β3 (3). Thus, in principle, topically applied α2-selective cardiac glycosides that penetrate the intact eye and reach the ciliary epithelium could effectively reduce IOP, and provided that they penetrate the intact eye and reach the ciliary epithelium, they could be applied topically. A potential advantage of topical application could be that systemic toxic effects typical of cardiac glycosides should be minimal.

Another possible application of an α2-selective cardiac glycoside could be as an effective cardiotonic drug, with reduced cardiotoxicity, compared to known drugs such as digoxin. *Digitalis* drugs such as digoxin have been used to treat heart failure for over two hundred years but are dangerous drugs with multiple side effects. There is now good evidence that selective inhibition of α2 is especially effective in enhancing cardiac excitation-contraction coupling and mediating cardiac glycoside-mediated positive inotropy (4). Inhibition of α2, which is a minor isoform, may not cause cellular Ca overload, the hallmark of cardiac toxicity (5).

The isoform selectivity of a large number of known cardiac glycosides has been previously studied (6), using the yeast *P. pastoris* expressing Na,K-ATPase isoforms (α1β1, α2β1, α3β1), and purified detergent-soluble isoform complexes of Na,K-ATPase (7-11). Dissociation constants, $K_D$, for digitalis glycosides, digoxin and digitoxin, measured in $^3$H-ouabain displacement assays in membranes, showed moderate selectivity (3-4-fold) for α2/α3 over α1. By contrast, aglycones such as digoxigenin and digitoxgenin showed no isoform selectivity. In assays of inhibition of Na,K-ATPase activity, measured with the purified isoform protein complexes, digoxin and digitoxin showed 3-4-fold lower Ki values for α2 compared to α1, with α3 more similar to α1. Again, no aglycones of any cardiac glycosides tested showed isoform selectivity. For digoxin derivatives, with one to four digitoxose moieties the maximal α2/α1 selectivity was found for digoxin itself, with three digitoxose sugars. By contrast to the digitalis glycosides, the $K_D$ of ouabain showed some preference for α1 over α2 and similar Ki values for all three isoforms.

Based on these studies, it was determined that the sugar moiety of digoxin likely determines isoform selectivity, which is generally consistent with recent structures of Na,K-ATPase with bound ouabain (12-14). The unsaturated lactone ring and steroid portion of ouabain are bound between trans-membrane segments M1, M4, M5 of the α subunit, in which there are no amino-acid differences between isoforms. Assuming that the aglycones of all cardiac glycosides bind similarly, the implication is that isoforms cannot discriminate between any of the aglycones, as found experimentally. By contrast, the sugar is bound near extracellular loops, where there are a number of amino-acid differences between the isoforms. These residues might interact with the sugars of bound digoxin in an isoform-selective way.

There is an unmet need for new therapies for treating ocular disorders associated with elevated intraocular pressure, such as glaucomas, and for new cardiotonic agents, that are effective on the one hand, and that demonstrate an acceptable safety profile on the other.

SUMMARY OF THE INVENTION

The present invention relates to digoxin and digitoxin derivatives that are selective inhibitors of the α2 isoform of Na,K-ATPase over other isoforms of this enzyme. The compounds of the invention effectively reduce intra-ocular pressure, and are useful in the treatment of disorders associated with elevated intraocular pressure, such as glaucomas, and/or as cardiotonic agents.

It has previously been shown, using recombinant human α1β1, α2β1 and α3β1 isoforms, that the classical inhibitor digoxin is partially α2-selective and that the tri-digitoxose moiety is responsible for isoform-selectivity. The present invention is based on the discovery that modification of the third digitoxose increases selectivity for α2 over α1. Thus, the third digitoxose of digoxin has been chemically modified by periodate oxidation and reductive amination using a variety of R—NH$_2$ substituents, leading to a series of perhydro-1,4-oxazepine derivatives of digoxin. As demonstrated herein for the first time, several derivatives show increased selectivity for α2 over α1, up to about 8-fold. Moreover, a molecular model of digoxin bound to the Na,K-ATPase suggests that perhydro-1,4-oxazepine derivatives of digoxin with different aliphatic substitutions could be relatively selective for the α2β3 complex. Indeed, a series of aliphatic derivatives show improved selectivity for α2β3 over α1β1-up to about 16-fold. Effects of topically applied cardiac glycosides on intra-ocular pressure in rabbits have been assessed by their ability to prevent or reverse an acute intraocular pressure increase induced by 4-aminopyridine or a selective agonist of the A3 adenosine receptor. The α2-selective digoxin/digitoxin derivatives prevent or reverse ocular hypertension more efficiently as compared with digoxin itself, digoxigenin or ouabain. The digoxin/digitoxin derivatives of the present invention thus have the utility in the treatment of disorders associated with elevated intraocular pressure, such as glaucomas. As demonstrated herein, the most α2β3-selective derivative is especially effective. These observations are consistent with a major role of α2β3 in aqueous humour production and suggest that, potentially, α2-selective and especially α2β3-selective digoxin derivatives could be of interest as novel drugs for control of intraocular pressure.

Moreover, the α2-selective digoxin/digitoxin derivatives of the present invention may show reduced toxicity, especially when applied topically. First, swelling of the cornea and lens should be minimal since only α1 and a minor amount of α3 but no α2 is expressed in the corneal epithelium and only α1 is expressed in the lens epithelium. Second, an α2-selective digoxin/digitoxin derivative that reaches the general circulation from the eye should be only minimally cardiotoxic. Thus the present invention provides compounds that are not only potent as IOP-reducing agent, but that have the potential to be significantly less toxic than the parent compounds digoxin or digitoxin.

According to one aspect, the present invention relates to a compound represented by the structure of general formula (I):

wherein
R is selected from the group consisting of OH, $C_1$-$C_6$ alkyl, $C_1$-$C_6$ haloalkyl, —$(CR^bR^c)_n Si(R^a)_3$, —$(CR^bR^c)_n$—C(=Y)—$NR^1R^2$, —$(CR^bR^c)_n$—C(=Y)—NHOH, —$(CR^dR^e)_n$—C(=Y)—COOR$^3$; and —NHC(=Y)NR$^1$R$^2$;
Y is O or S;
X is H or OH;
R$^1$, R$^2$ and R$^3$ are each independently H or a $C_1$-$C_4$ alkyl;
R$^a$ is a $C_1$-$C_4$ alkyl;
R$^b$, R$^c$ and R$^d$ are each independently selected from H, a $C_1$-$C_4$ alkyl and a $C_1$-$C_4$ hydroxy alkyl;
R$^e$ is selected from a $C_1$-$C_4$ alkyl and a $C_1$-$C_4$ hydroxyalkyl; and
n is 0, 1 or 2;
including salts, hydrates, solvates, polymorphs, geometrical isomers, optical isomers, enantiomers, diastereomers, and mixtures thereof.

In one embodiment of formula (I), R is selected from the group consisting of CZ$_3$, —CZ$_2$CZ$_3$, —(CH$_2$)$_2$CH$_3$, —CH(CH$_3$)$_2$, —(CH$_2$)$_3$CH$_3$, —CH$_2$CH(CH$_3$)$_2$, —CH(CH$_3$)CH$_2$CH$_3$ and —C(CH$_3$)$_3$, wherein each Z is independently at each occurrence H or halogen. In one particular embodiment each Z is H or F.

In another embodiment of formula I, R is selected from the group consisting of —CH$_2$—C(=O)—NH$_2$, —CH$_3$, —(CH$_2$)$_2$—C(=O)—NH$_2$, —NHC(=O)—NH$_2$, OH, —CH(CH$_3$)CONH$_2$, —CH(CH$_2$OH)COOH, —CH(CH$_2$OH)CONH$_2$, —CH$_2$CH$_3$, —CH$_2$CH$_2$CH$_3$, —CH$_2$C(CH$_3$)$_2$, —CH$_2$CF$_3$, —CH$_2$CONHOH, —NHCSNH$_2$, —CH$_2$CH$_2$F, —CH(CH$_2$)$_3$, —C(CH$_3$)$_3$, and —CH$_2$—Si(CH$_3$)$_3$. Each possibility represents a separate embodiment of the present invention.

In one embodiment of formula (I), R$^1$, R$^2$ and R$^3$ are each H. In another embodiment of formula (I), n is 1. In another embodiment of formula (I), n is 2. In another embodiment of formula (I), Y is O. In another embodiment of formula (I), Y is S. In another embodiment of formula I, the $C_1$-$C_4$ hydroxyalkyl is CH$_2$OH (i.e., the compound is derived from serine or serinamide).

In one currently preferred embodiment, the compounds of the invention are derivatives of digoxin, i.e., X is OH in Formula I. In one embodiment, the present invention relates to a compound of formula I wherein X is OH and R is —CH$_2$—C(=O)—NH$_2$ (designated herein "DGlyN" or

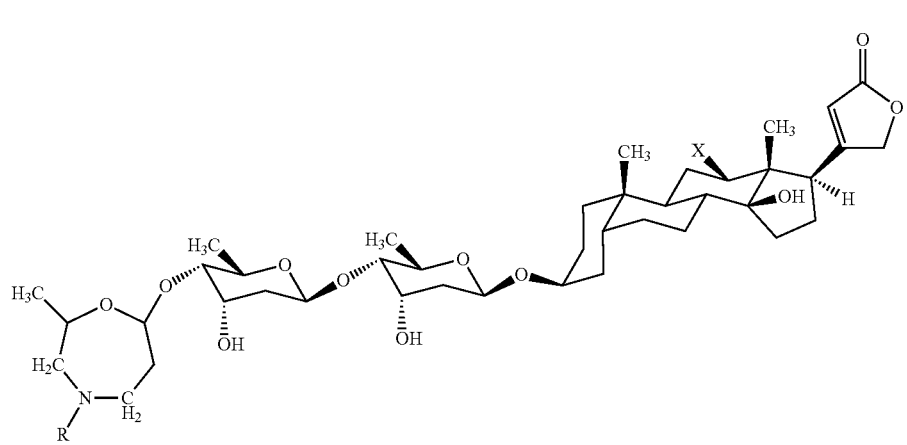

"compound 1"). In another embodiment, the present invention relates to a compound of formula I wherein X is OH and R is —CH₃ (designated herein "DMe" or "compound 2"). In another embodiment, the present invention relates to a compound of formula I wherein X is OH and R is —(CH₂)₂—C(=O)—NH₂ (designated herein "DPrN" or "compound 3"). In another embodiment, the present invention relates to a compound of formula I wherein X is OH and R is —NHC(=O)—NH₂ (designated herein "DSCar" or "compound 4"). In another embodiment, the present invention relates to a compound of formula I wherein X and R are each OH (compound 6). In another embodiment, the present invention relates to a compound of formula I wherein X is OH and R is —CH(CH₃)CONH₂ (compound 8). In another embodiment, the present invention relates to a compound of formula I wherein X is OH and R is —CH(CH₂OH)COOH (compound 9). In another embodiment, the present invention relates to a compound of formula I wherein X is OH and R is —CH(CH₂OH)CONH₂ (compound 10). In another embodiment, the present invention relates to a compound of formula I wherein X is OH and R is —CH₂CH₃ (compound 12). In another embodiment, the present invention relates to a compound of formula I wherein X is OH and R is —(CH₂)₂CH₃ (compound 13). In another embodiment, the present invention relates to a compound of formula I wherein X is OH and R is —CH₂CH(CH₃)₂ (compound 14). In another embodiment, the present invention relates to a compound of formula I wherein X is OH and R is —CH₂CF₃ (designated herein "DMeCF₃" or "compound 15"). In another embodiment, the present invention relates to a compound of formula I wherein X is OH and R is —CH₂C(=O)—NHOH (compound 17). In another embodiment, the present invention relates to a compound of formula I wherein X is OH and R is —NHCSNH₂ (compound 18). In another embodiment, the present invention relates to a compound of formula I wherein X is OH and R is —CH₂CH₂F (compound 19). In another embodiment, the present invention relates to a compound of formula I wherein X is OH and R is —CH(CH₃)₂ (compound 21). In another embodiment, the present invention relates to a compound of formula I wherein X is OH and R is —C(CH₃)₃ (compound 22). In another embodiment, the present invention relates to a compound of formula I wherein X is OH and R is —CH₂—Si(CH₃)₃ (compound 23).

In another currently preferred embodiment, the compounds of the invention are derivatives of digitoxin, i.e., X is H in Formula I.

In one embodiment, the compound of the present invention is selective for α2 isoform of Na,K-ATPase over other isoforms of Na,K-ATPase. In other embodiments, the compound of the present invention is selective for the α2β1, α2β2 and/or α2β3 isoform of Na,K-ATPase over the α1β1 isoform of Na,K-ATPase, with each possibility representing a separate embodiment of the present invention.

In other embodiments, the present invention relates to a pharmaceutical composition comprising a compound of formula (I), and a pharmaceutically acceptable carrier or excipient. In some preferred embodiments, the pharmaceutical composition is an ophthalmic composition suitable for topical application to the eye in the form of an eye-drop solution, an ointment, a suspension, a gel or a cream. Each possibility represents a separate embodiment of the present invention.

Preferably, the composition further comprises at least one pharmaceutically acceptable agent selected from one or more of a stabilizer, a preservative, a chelating agent, a viscosity modifying agent, a buffering agent, and pH adjusting agent. Each possibility represents a separate embodiment of the present invention.

The compounds of the present invention are preferably selective for α2 isoform of Na,K-ATPase over other isoforms of Na,K-ATPase, i.e., they inhibit the α2 isoform (especially the α2β3 isoform) over other isoforms of this enzyme, e.g., the α1 isoform. As such, they are useful in methods for reducing ocular hypertension, or for treating diseases associated with ocular hypertension, such as glaucoma. Thus, in one embodiment, the present invention relates to a method for reducing ocular hypertension, or for treating conditions associated with ocular hypertension such as glaucoma, by administering to a subject in need of such a treatment an effective amount of a compound of formula I or a pharmaceutical composition according to the present invention. In other embodiments, the compound useful for reducing ocular hypertension, or for treating conditions associated with ocular hypertension such as glaucoma, is a compound of formula IA:

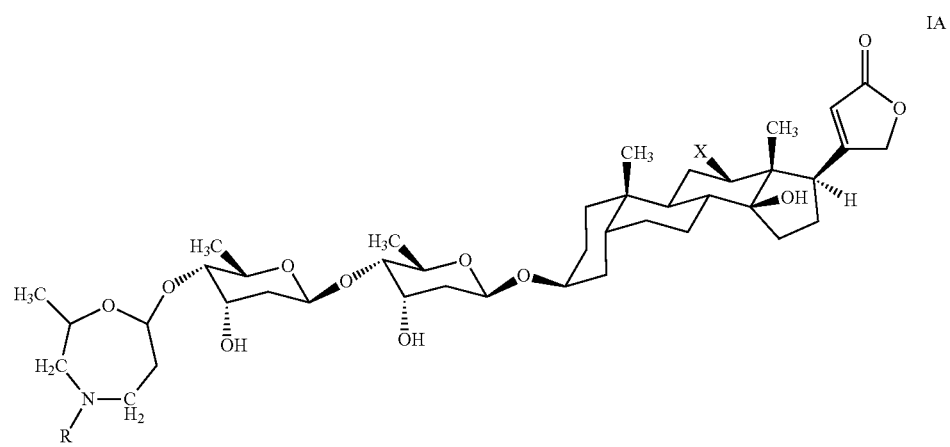

IA wherein
  R is selected from the group consisting of OH, $C_1$-$C_6$ alkyl, $C_1$-$C_6$ haloalkyl, —$(CR^bR^c)_n Si(R^a)_3$, —$(CR^bR^c)_n$—C(=Y)—$NR^1R^2$, —$(CR^bR^c)_n$—C(=Y)—NHOH, —$(CR^dR^e)_n$—C(=Y)—$COOR^3$; —NHC(=Y)$NR^1R^2$; and —$(CR^bR^c)_n$—$NH_2$;
  Y is O or S;
  X is H or OH;
  $R^1$, $R^2$ and $R^3$ are each independently H or a $C_1$-$C_4$ alkyl;
  $R^a$ is a $C_1$-$C_4$ alkyl;
  $R^b$, $R^c$, $R^d$ and $R^e$ are each independently selected from H, a $C_1$-$C_4$ alkyl and a $C_1$-$C_4$ hydroxy alkyl; and
  n is 0, 1 or 2;
    including salts, hydrates, solvates, polymorphs, geometrical isomers, optical isomers, enantiomers, diastereomers, and mixtures thereof.

In one embodiment of formula (I), R is selected from the group consisting of $CZ_3$, —$CZ_2CZ_3$, —$(CH_2)_2CH_3$, —$CH(CH_3)_2$, —$(CH_2)_3CH_3$, —$CH_2CH(CH_3)_2$, —$CH(CH_3)CH_2CH_3$ and —$C(CH_3)_3$, wherein each Z is independently at each occurrence H or halogen. In one particular embodiment each Z is H or F.

In another embodiment of formula (IA), R is selected from the group consisting of —$CH_2$—C(=O)OH, —$CH_2$—C(=O)—$OCH_3$ and $CH_2$—$CH_2$—$NH_2$. Each possibility represents a separate embodiment of the present invention.

In one embodiment of formula (IA), $R^1$ and $R^2$ are each H. In one embodiment of formula (IA), $R^3$ is H or $CH_3$. In another embodiment of formula (IA), n is 1. In another embodiment of formula (IA), n is 2. In another embodiment of formula (IA), Y is O. In another embodiment of formula (IA), Y is S. In another embodiment of formula (IA), the $C_1$-$C_4$ hydroxyalkyl is $CH_2OH$ (i.e., the compound is derived from serine or serinamide).

In one currently preferred embodiment, the compounds of the invention are derivatives of digoxin, i.e., X is OH in Formula IA. In one embodiment, the present invention relates to a compound of formula IA wherein X is OH and R is —$CH_2$—C(=O)OH (designated herein "DGly" or "compound 5"). In another embodiment, the present invention relates to a compound of formula IA wherein X is OH and R is —$CH_2$—C(=O)—$OCH_3$ (designated herein "DGlyMe" or compound 7). In another embodiment, the present invention relates to a compound of formula IA wherein X is OH and R is —$CH_2$—$CH_2$—$NH_2$ (designated herein "DEtDA or compound 11").

In another currently preferred embodiment, the compounds of the invention are derivatives of digitoxin, i.e., X is H in Formula IA.

The compound of formula IA may be administered in a pharmaceutical composition as described above for formula I. In some embodiments, the compounds encompassed by formula IA are selective for α2 isoform of Na,K-ATPase over other isoforms of Na,K-ATPase, i.e., they inhibit the α2 isoform over other isoforms of this enzyme, e.g., the α1 isoform. In other embodiments, the compounds encompassed by formula IA are selective for the α2β1, α2β2 and/or α2β3 isoform of Na,K-ATPase over the α1β1 isoform of Na,K-ATPase, with each possibility representing a separate embodiment of the present invention.

In other embodiments, the present invention relates to the use of a compound of formula I or IA, or any compound encompassed by such formulae, for the manufacture of a medicament for the reduction of ocular hypertension, or for treating diseases or disorders associated with ocular hypertension, such as glaucoma. Each possibility represents a separate embodiment of the present invention.

In other embodiments, the compounds of the invention are also useful as cardiotonic agents. Thus, in one embodiment, the present invention relates to a cardiotonic composition comprising of a compound of formula (I), or a compound of formula (IA). In another embodiment, the present invention relates to the use of a compound of formula (I) or formula (IA), as a cardiotonic agent. Each possibility represents a separate embodiment of the present invention.

The present invention will be better understood in conjunction with the description, figures and claims below.

BRIEF DESCRIPTION OF THE DRAWINGS

FIG. 2B: Reverse phase HPLC purification of DGlyN, a representative compound of the present invention.

FIG. 6 depicts the change in IOP (in mmHg) after 1.5 hours administration of 4AP and 0.1 mM CG. FIG. 6 represents an average of 3 different experiments with the SEM.

FIG. 8A. DMe at the indicated concentrations was added 30 minutes prior to IB-MECA. FIG. 8B. Digoxigenin, DGlyN, or DMe, 1 mM were added 1.5 hours after the first addition of IB-MECA. FIG. 8C. Digoxigenin or DGlyN, 3 mM were added 1.5 hours after the first addition of IB-MECA. 1 μM IB-MECA was added at time zero and every 2 hours thereafter (arrows).

FIG. 9 depicts normalized data from representative experiments using the four different cardiac glycosides, obtained as described in the Methods.

FIG. 10A. The model depicts the porcine α1β1 complex (4HYT) with bound digoxin (3B0W). FIG. 10B. Detail of residues in proximity to bound digoxin (numbering is for porcine α1 and β1). FIG. 10C and FIG. 10D depict β1 versus β3 showing β1Gln84 and βVal89.

FIG. 12 shows representative curves.

FIG. 13 shows representative curves.

FIG. 14 shows representative curves.

FIG. 15 represents the average effects of different concentrations of DIB in four experiments.

DETAILED DESCRIPTION OF THE INVENTION

Figure 1:
FIG. 1 Technical features of the ocular hypertension experiments. New Zealand white rabbits were used for IOP measurements, IOP (mm Hg) of rabbits was measured using a calibrated Pneumatonometer (Model 30, Reichert technologies).
Figure 1:
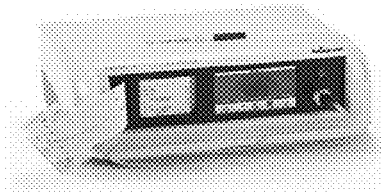

Unless otherwise specified, "a" or "an" means "one or more".

The present invention relates to digoxin and digitoxin derivatives that are selective inhibitors of the α2 isoform of Na,K-ATPase. The compounds of the invention effectively reduce intra-ocular pressure, and are useful in the treatment of disorders associated with elevated intraocular pressure, such as glaucomas, and/or as cardiotonic agents.

The term "selective inhibitor of the α2 isoform of Na,K-ATPase" means that the compound inhibits the α2 isoform of Na,K-ATPase to a greater degree than the other isoforms, e.g., the α1. In some embodiments, the compounds described herein are selective for the α2β1, α2β2 and/or α2β3 isoform of Na,K-ATPase over the α1β1 isoform of Na,K-ATPase. In some embodiments, the selectivity of the compound for the α2 isoform of Na,K-ATPase (e.g., α2β1, α2β2 and/or α2β3 isoform) is up to about 20 fold over other isoforms, e.g., up to 16 fold, 8 fold, 5 fold or 2 fold greater inhibition of the α1 isoform over other isoforms of this enzyme.

Compounds

According to one aspect, the present invention relates to a compound represented by the structure of general formula (I):

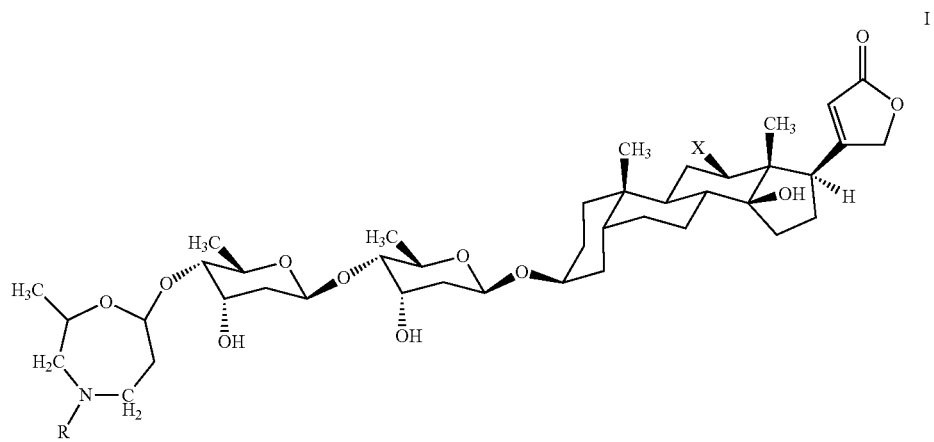

wherein

R is selected from the group consisting of OH, $C_1$-$C_6$ alkyl, $C_1$-$C_6$ haloalkyl, —$(CR^bR^c)_n Si(R^a)_3$, —$(CR^bR^c)_n$—C(=Y)—$NR^1R^2$, —$(CR^bR^c)_n$—C(=Y)—NHOH, —$(CR^dR^e)_n$—C(=Y)—$COOR^3$; and —NHC(=Y)$NR^1R^2$;

Y is O or S;

X is H or OH;

$R^1$, $R^2$ and $R^3$ are each independently H or a $C_1$-$C_4$ alkyl;

$R^a$ is a $C_1$-$C_4$ alkyl;

$R^b$, $R^c$ and $R^d$ are each independently selected from H, a $C_1$-$C_4$ alkyl and a $C_1$-$C_4$ hydroxy alkyl;

$R^e$ is selected from a $C_1$-$C_4$ alkyl and a $C_1$-$C_4$ hydroxyalkyl; and n is 0, 1 or 2;

including salts, hydrates, solvates, polymorphs, geometrical isomers, optical isomers, enantiomers, diastereomers, and mixtures thereof.

According to another aspect, the present invention relates to a compound represented by the structure of general formula (IA):

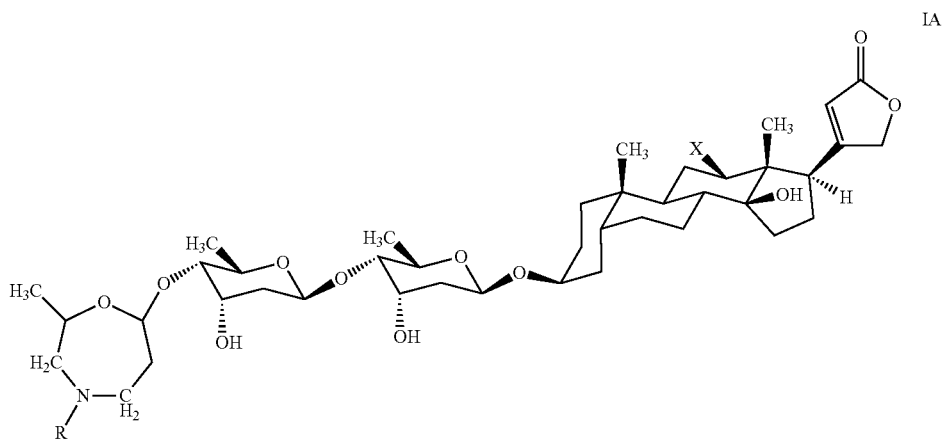

wherein

R is selected from the group consisting of OH, $C_1$-$C_6$ alkyl, $C_1$-$C_6$ haloalkyl, —$(CR^bR^c)_n$Si$(R^a)_3$, —$(CR^bR^c)_n$—C(=Y)—NR$^1$R$^2$, —$(CR^bR^c)_n$—C(=Y)—NHOH, —$(CR^dR^e)_n$—C(=Y)—COOR$^3$; —NHC(=Y)NR$^1$R$^2$; and —$(CR^bR^c)_n$—NH$_2$;

Y is O or S;

X is H or OH;

R$^1$, R$^2$ and R$^3$ are each independently H or a $C_1$-$C_4$ alkyl;

R$^a$ is a $C_1$-$C_4$ alkyl;

R$^b$, R$^c$, R$^d$ and R$^e$ are each independently selected from H, a $C_1$-$C_4$ alkyl and a $C_1$-$C_4$ hydroxy alkyl; and n is 0, 1 or 2; including salts, hydrates, solvates, polymorphs, geometrical isomers, optical isomers, enantiomers, diastereomers, and mixtures thereof.

In some currently preferred embodiment, the compound is selected from the group consisting of a digoxin derivative (X is OH) or a digitoxin derivative (X is H). Several preferred compounds of formula (I) or (IA) are exemplified below, with each possibility representing a separate embodiment of the present invention.

A compound of formula (1), in which X is OH and R is derived from glycinamide (R==—CH$_2$C(=O)—NH$_2$), abbreviated herein "DGlyN".

A compound of formula (2), in which X is OH and R is CH$_3$, abbreviated herein "DMe".

A compound of formula (3), in which X is OH and R is derived from propionamide (R==—CH$_2$CH$_2$C(=O)—NH$_2$), abbreviated herein "DPrN".

A compound of formula (4), in which X is OH and R is derived from semicarbazide (R==—NHC(=O)—NH$_2$), abbreviated herein "DSCar".

A compound of formula (5), in which X is OH and R is derived from glycine (R==—CH$_2$C(=O)OH), abbreviated herein "DGly".

A compound of formula (6), in which X and R are each is OH, abbreviated herein "DOH".

A compound of formula (7), in which X is OH and R is derived from glycine methyl ester (R==—CH$_2$—C(=O)—OCH$_3$), abbreviated herein "DGlyMe".

A compound of formula (8), in which X is OH and R is derived from alanineamide (R==—CH(CH$_3$)CONH$_2$), abbreviated herein "DAlaN".

A compound of formula (9), in which X is OH and R is derived from serine (R ==—CH(CH$_2$OH)COOH), abbreviated herein "DSer".

A compound of formula (10), in which X is OH and R is derived from serinamide (R==—CH(CH$_2$OH)CONH$_2$), abbreviated herein "DSerN".

A compound of formula (11), in which X is OH and R is derived from ethylene diamine (R==—CH$_2$—CH$_2$—NH$_2$), abbreviated herein "DEtDA".

A compound of formula (12), in which X is OH and R is —CH$_2$CH$_3$ abbreviated herein "DEt".

A compound of formula (13), in which X is OH and R is —(CH$_2$)$_2$CH$_3$ abbreviated herein "DPr" or "DP".

A compound of formula (14), in which X is OH and R is —CH$_2$CH(CH$_3$)$_2$ abbreviated herein "DiBu".

A compound of formula (15), in which X is OH and R is derived from 2,2,2-trifluoroethyl (R==—CH$_2$CF$_3$), abbreviated herein "DMeCF$_3$".

A compound of formula (17) wherein X is OH and R is —CH$_2$C(=O)—NHOH, abbreviated herein "DGlyNHOH".

A compound of formula (18) wherein X is OH and R is derived from semithiocarbazide (R==—NHCSNH$_2$), abbreviated herein "DSSCar".

A compound of formula (19) wherein X is OH and R is —CH$_2$CH$_2$F, abbreviated herein "DCH$_2$CH$_2$F".

A compound of formula (21) wherein X is OH and R is —CH(CH$_3$)$_2$, abbreviated herein "DiPro" or "DIP".

A compound of formula (22) wherein X is OH and R is —C(CH$_3$)$_3$, abbreviated herein "DtBu".

A compound of formula (23) wherein X is OH and R is methyl (trimethylsilyl) (—CH$_2$Si(CH$_3$)$_3$), abbreviated herein "DTMS".

These and other representative compounds are shown hereinbelow in Table 1.

The term "$C_1$-$C_6$ alkyl" group refers to any saturated aliphatic hydrocarbon, including straight-chain and branched-chain groups containing between 1 and 6 carbon atoms. The term "$C_1$-$C_4$ alkyl" group refers to any saturated aliphatic hydrocarbon, including straight-chain and branched-chain groups containing between 1 and 4 carbon atoms. Non-limiting examples of alkyl groups include methyl, ethyl, propyl, isopropyl, n-butyl, sec-butyl, t-butyl, n-pentyl, 2-pentyl, 3-pentyl, neopentyl, 1-hexyl, 2-hexyl and 3-hexyl. The alkyl group may be substituted or unsubstituted.

The term "halogen" refers to fluoro, chloro, bromo or iodo.

All stereoisomers, optical and geometrical isomers of the compounds of the instant invention are contemplated, either in admixture or in pure or substantially pure form. The compounds of the present invention can have asymmetric centers at one or more of the atoms. Consequently, the compounds can exist in enantiomeric or diastereomeric forms or in mixtures thereof. The present invention contemplates the use of any racemates (i.e. mixtures containing equal amounts of each enantiomers), enantiomerically enriched mixtures (i.e., mixtures enriched for one enantiomer), pure enantiomers or diastereomers, or any mixtures thereof. The chiral centers can be designated as R or S or R,S or d,D, l,L or d,l, D,L. Compounds comprising amino acid residues (e.g., glycine or glycinamide) include residues of D-amino acids, L-amino acids, or racemic derivatives of amino acids.

One or more of the compounds of the invention, may be present as a salt. The term "salt" encompasses both basic and acid addition salts, and include salts formed with organic and inorganic anions and cations. The term "organic or inorganic cation" refers to counter-ions for an acid. The counter-ions can be chosen from the alkali and alkaline earth metals, (such as lithium, sodium, potassium, barium, aluminum and calcium), ammonium and the like. Furthermore, the term includes salts that form by standard acid-base reactions of basic groups and organic or inorganic acids. Such acids include hydrochloric, hydrofluoric, hydrobromic, trifluoroacetic, sulfuric, phosphoric, acetic, succinic, citric, lactic, maleic, fumaric, cholic, pamoic, mucic, D-camphoric, phthalic, tartaric, salicylic, methanesulfonic, benzenesulfonic, p-toluenesulfonic, sorbic, picric, benzoic, cinnamic, and like acids.

The present invention also includes solvates of the compounds of the present invention and salts thereof. "Solvate" means a physical association of a compound of the invention with one or more solvent molecules. This physical association involves varying degrees of ionic and covalent bonding, including hydrogen bonding. In certain instances the solvate will be capable of isolation. "Solvate" encompasses both solution-phase and isolatable solvates. Non-limiting examples of suitable solvates include ethanolates, methanolates and the like. "Hydrate" is a solvate wherein the solvent molecule is water.

The present invention also includes polymorphs of the compounds of the present invention and salts thereof. The term "polymorph" refers to a particular crystalline state of a substance, which can be characterized by particular physical properties such as X-ray diffraction, IR spectra, melting point, and the like.

Pharmaceutical Compositions and Therapeutic Uses

In some embodiments, the present invention provides a method for treating disorders associated with elevated intraocular pressure, and in particular for treating glaucoma, by administering an effective amount of a pharmaceutical compositions comprising a compound of formula I and/or IA as the active ingredient (e.g., compounds 1, 2, 3, 4, 5, 6, 7, 8, 9, 10, 11, 12, 13, 14, 15, 17, 18, 19, 21, 22 or 23) and a pharmaceutically acceptable carrier.

In other embodiments, the present invention provides a method for reducing elevated intraocular pressure, by administering an effective amount of a pharmaceutical composition comprising a compound of formula I and/or IA as the active ingredient (e.g., compounds 1, 2, 3, 4, 5, 6, 7, 8, 9, 10, 11, 12, 13, 14, 15, 17, 18, 19, 21, 22 or 23) and a pharmaceutically acceptable carrier.

Preferably, the pharmaceutical compositions of the invention is an ophthalmic composition which is administered topically onto the eye of a patient for facilitating effective intraocular levels of the drug and for preventing unnecessary drug level in other organs. Such a non-systemic, site-specific administration reduces the side effects associated with the drugs. However, oral or otherwise systemic administration in a dosage effective for reducing the intraocular pressure is also possible. For example, the composition may be administered by a dermal patch for extended release.

When administration is topical, the pharmaceutical compositions containing the digoxin derivative of formula I or IA may be formulated in various therapeutic forms suitable for topical delivery, including solutions, suspensions, emulsions and gels. The carrier in these formulations may be any pharmaceutical acceptable carrier such as saline, buffered saline, carbopol gel, mineral oil and the like. The formulations can be prepared in accordance with known procedures for the preparation of ophthalmic formulations. Preferably, the concentration of the digoxin derivative in the pharmaceutical compositions is in the range of about 1 to about 5,000 µg/ml, preferably from about 80 to about 800 µg/ml and the formulation is preferably applied in one to four doses per day wherein each dose contains about 1 to 125 µg of the digoxin derivative, more preferably from about 2 to about 20 µg of digoxin derivative.

The topical pharmaceutical compositions may be in the form of eye-drops to be applied by instillation into the eye or may be in the form of a viscous ointment, gel or cream to be applied by an ointment onto the ocular surface and may contain control release means for facilitating sustained release over a prolonged period of time.

The compositions may further include non-toxic auxiliary pharmaceutically acceptable substances such as stabilizers, preservatives, chelating agents, viscosity modifying agents, buffering agents and/or pH adjusting agents. Additionally, the compositions may contain other ophthalmic active agents such as antibacterial agents, comfort enhancers, antioxidants, intra-ocular pressure (IOP)-reducing drugs and the like.

In accordance with other embodiments, the digoxin/digitoxin derivative may be loaded into a drug-delivery device to be inserted or implanted into the eye of the patient for allowing releasing of the drug in a controlled and continuous rate, by dissolving, diffusion or leaching, thus maintaining effective therapeutic concentration over a prolonged period of time. The drug-delivery device may be for example a biocompatible thin film loaded with the active agent, inserted for example beneath the lower eyelid.

Another possible application of an α2-selective cardiac glycoside is as an effective cardiotonic drug, with reduced cardiotoxicity, compared to known drugs such as digoxin. Thus, in other embodiments, the present invention provides cardiotonic compositions comprising a compound of formula I and/or IA as the active ingredient (e.g., compounds 1, 2, 3, 4, 5, 6, 7, 8, 9, 10, 11, 12, 13, 14, 15, 17, 18, 19, 21, 22 or 23) and a pharmaceutically acceptable carrier. In accordance with this embodiment, the compounds according to the invention may therefore be formulated for oral, buccal, topical, parenteral or rectal administration.

For oral administration, the composition may be provided, for example, in the form of tablets, capsules, powders, solutions, syrups or suspensions prepared by conventional methods using acceptable diluents. For buccal administration, the composition may be provided in the form of conventionally formulated tablets or sachets.

The compounds according to the invention may be formulated for parenteral administration by bolus injection or continuous infusion. Formulations for injection may be provided in the form of ampoules containing single doses or they may be provided in multiple dose containers with added preservative. The composition may be in the form of suspensions, solutions and the like.

Alternatively, the active ingredient may be provided in powder form to be reconstituted before use with a suitable carrier. For topical use, the compounds according to the invention may be formulated in the conventional manner as ointments, creams, gels, lotions, powders or sprays.

The principles of the invention, using an albumin conjugate isoflavone derivative bound to a bioactive moiety such as an imaging agent or a therapeutic agent for selective delivery to cells susceptible to isoflavone according to the present invention, may be better understood with reference to the following non-limiting examples.

full assignments were obtained for several derivatives and will be published elsewhere. Structures of representative compounds of the invention are shown in Table 1. For verification of the structures, masses of the purified compounds were then determined. The table shows the structures of the different amine substituents, names, and theoretical and experimentally found masses of fifteen digoxin derivatives, and also the glycine derivative of bis-digitoxose digoxigenin. Mass spectra were obtained in a Micromass ZQ 4000 spectrometer, with Electro Spray Ionization.

TABLE 1

Structures, names and masses of perhydro-1,4-oxazepine derivatives of digoxin

| R = | Derivative Chem. Name | Name Abbreviation | Theoretical Exact Mass | Mass Found (M + Na$^+$) |
|---|---|---|---|---|
| —CH$_2$CONH$_2$ (1) | glycinamide | DGlyN | 820.47 | 843.42 |
| —CH$_3$ (2) | methylamine | DMe | 777.47 | 800.57 |
| —CH$_2$CH$_2$CONH$_2$ (3) | propionamide | DPrN | 834.49 | 857.30 |
| —NHCONH$_2$ (4) | semicarbazide | DSCar | 821.47 | 844.37 |
| —CH$_2$COOH (5) | glycine | DGly | 821.46 | 844.44 |
| —OH (6) | hydroxylamine | DOH | 779.45 | 802.47 |
| —CH$_2$COOCH$_3$ (7) | glycine methyl ester | DGlMe | 835.47 | 858.51 |
| —CH(CH$_3$)CONH$_2$ (8) | alaninamide | DAlaN | 834.49 | 857.56 |
| —CH(CH$_2$OH)COOH (9) | serine | DSer | 851.47 | 874.61 |
| —CH(CH$_2$OH)CONH$_2$ (10) | serinamide | DSerN | 850.48 | 873.59 |
| —CH$_2$CH$_2$NH$_2$ (11) | ethylenediamine | DEtDA | 806.49 | 829.48 |
| —CH$_2$CH$_3$ (12) | ethylamine | DEt | 791.48 | 814.52 |
| —CH$_2$CH$_2$CH$_3$ (13) | propylamine | DPr | 805.50 | 828.27 |
| —CH$_2$C(CH$_3$)$_2$ (14) | isobutylamine | DiBu | 819.51 | 842.41 |
| —CH$_2$CF$_3$ (15) | 2,2,2-trifluoroethylamine | DMeCF$_3$ | 845.45 | 868.14 |
| bis-CH$_2$COOH (16) | bis-glycine* | DbisGly | 691.39 | 714.40 |
| —CH$_2$CONHOH (17) | glycine hydroxamate | DGlyNHOH | 836.47 | 858.51 |
| —NHCSNH$_2$ (18) | semithiocarbazide | DSSCar | 821.47 | 844.37 |
| —CH$_2$CH$_2$F (19) | 2-fluoroethylamine | DCH$_2$CH$_2$F | 809.47 | 832.46 |
| —CH(CH$_2$)$_3$ (21) | isopropylamine | DiPro | 805.50 | 828.53 |
| —C(CH$_3$)$_3$ (22) | t-butylamine | DtBu | 819.51 | 842.66 |
| —CH$_2$Si(CH$_3$)$_3$ (23) | (Trimethylsilyl)methylamine | DTMS | 849.51 | 872.50 |

*bis-glycine refers to a glycine derivative of bis-digitoxose digoxigenin.

EXAMPLES

Figure 2A:
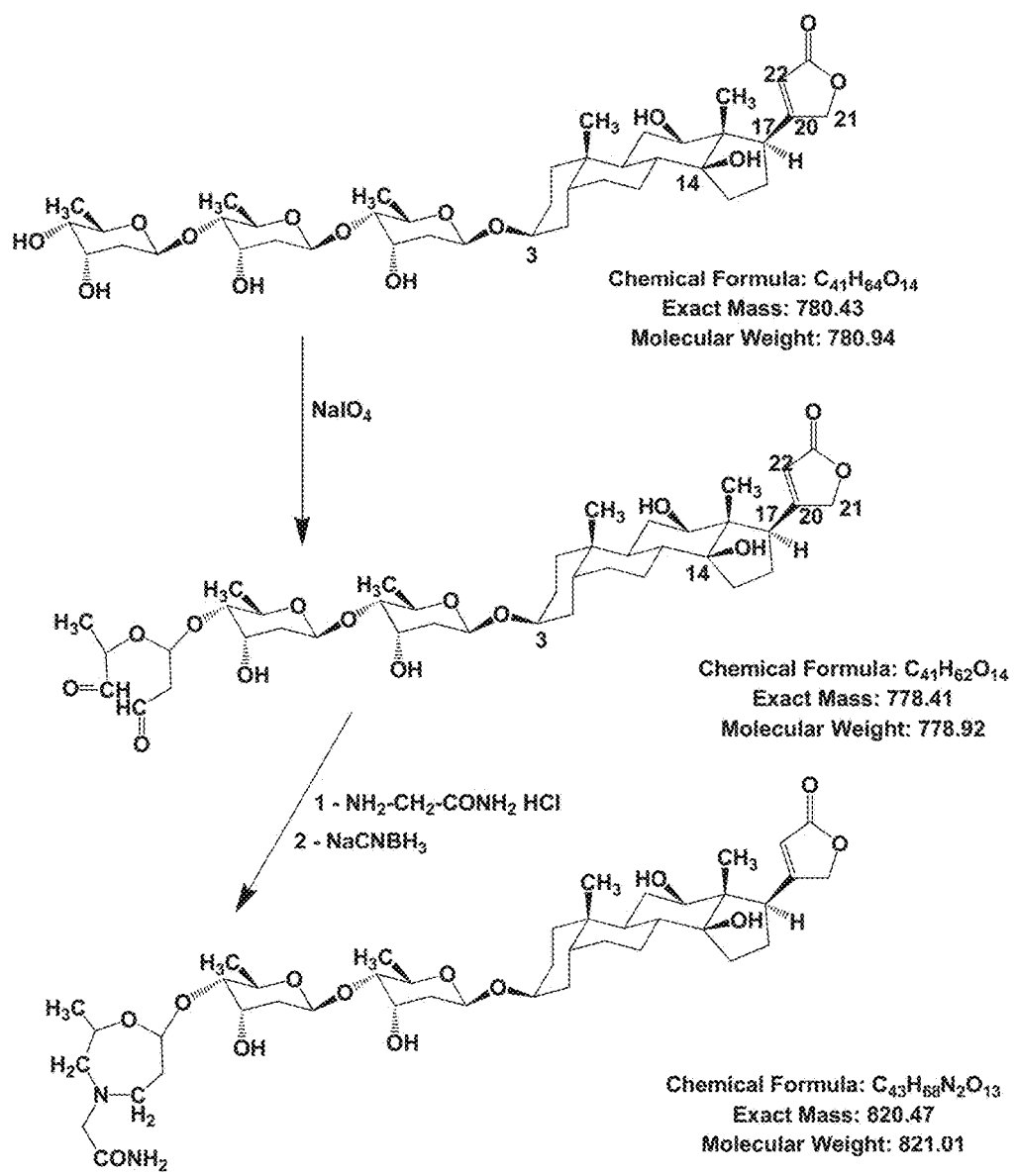
FIGS. 2A-B FIG. 2A: Synthesis of perhydro-1,4-oxazepine derivatives of digoxin.
Figure 2B:
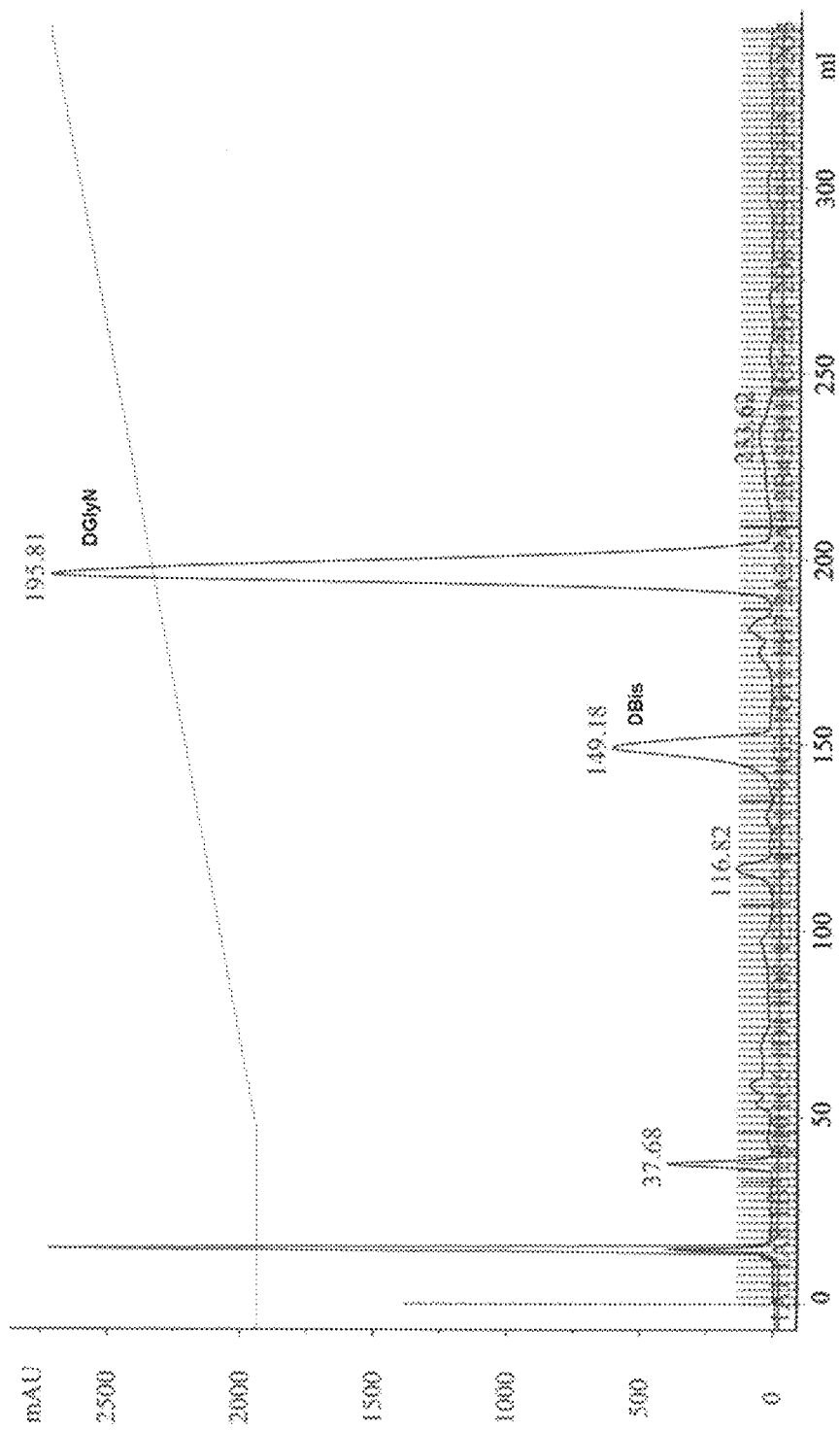
Figure 3A:
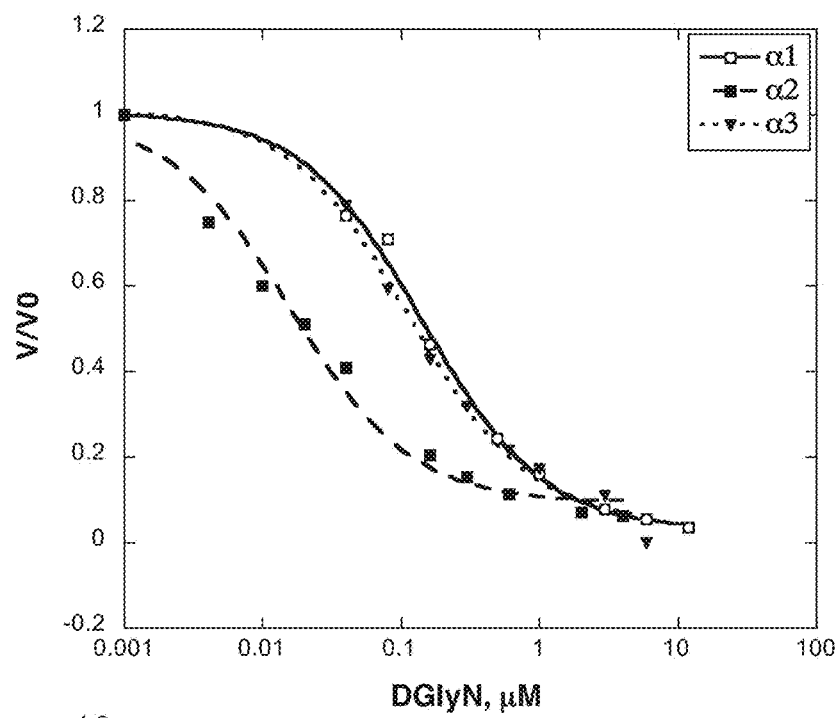
FIGS. 3A-B Inhibition of Na,K-ATPase activity of purified isoform complexes by digoxin derivatives. Representative experiments for inhibition of Na,K-ATPase activity by DGlyN (FIG. 3A) DMe (FIG. 3B). α1/β1 isoform □; α2/β1 isoform ■; α3/β1 isoform ▼. Lines are the fitted curves for a one-site inhibition model (see Example 4: Experimental Section).
Figure 3B:
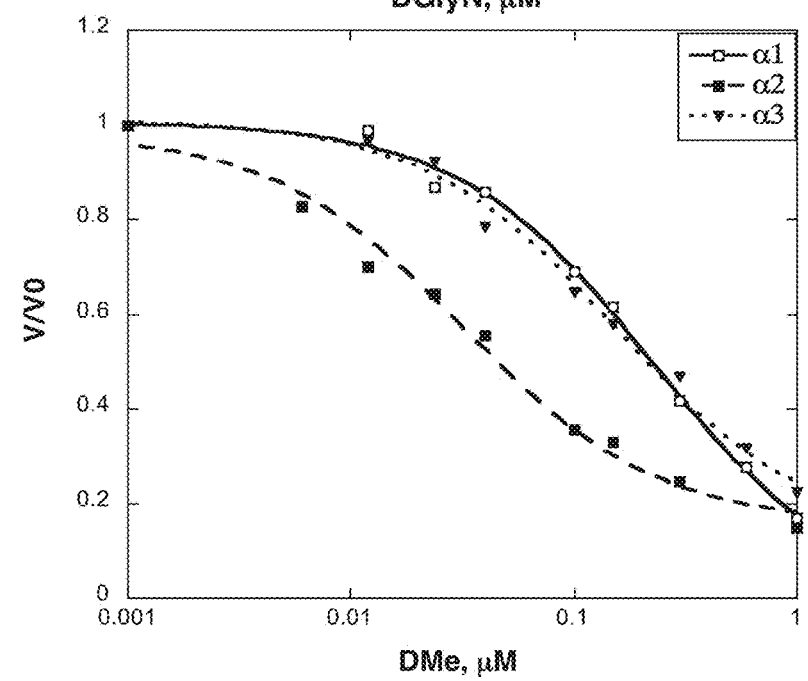

Example 1: Synthesis and Testing of Perhydro-1,4-Oxazepine Derivatives of Digoxin Perhydro-1,4-oxazepine derivatives were prepared according to the method described in (15). FIG. 2A shows the synthetic route involving (a) selective periodate oxidation of the third digitoxose moiety and (b) reductive amination of the dialdehyde using the free amine (R—NH$_2$) plus NaCNBH$_3$, for the case of glycinamide. Compounds were purified by HPLC, as seen for the representative example of the DGlyN derivative in FIG. 2B. Progress of both stages of the reactions as well as purification of compounds was monitored routinely by thin layer chromatography and mass spectrometry measurements. $^1$H and 13C NMR spectra and Example 2: Inhibition of Na,K-ATPase Activity FIGS. 3A-B show curves for inhibition of Na,K-ATPase activity of purified human isoforms ($\alpha 1\beta 1$, $\alpha 2\beta 1$ and $\alpha 3\beta 1$) of two derivatives, DGlyN (FIG. 3A) and DMe (FIG. 3B), with improved selectivity for $\alpha 2$ compared to digoxin itself. Table 2 provides information on the inhibitory effects of sixteen digoxin perhydro-1-4-oxazepine derivatives, in accordance with the present invention. The data in Table 2 show that the isoform selectivity ratios (Ki$\alpha 1/\alpha 2$) of several derivatives: DGlyN (7.45±0.46), DMe (6.47±0.71), DGly (5.1±0.54), DPrN (5.28±0.75) and DSCar (4.98±1.2) are significantly greater than that of digoxin (3.44±0.34). For these compounds, the Ki values for both $\alpha 1$ and $\alpha 2$ are lower than for digoxin, but the effect is greater for $\alpha 2$ compared to $\alpha 1$. Consequently, the ratio Ki $\alpha 1/\alpha 2$ is higher for the compounds of the invention compared to digoxin. In all cases the Ki for $\alpha 3$ is closer to that for $\alpha 1$ than to $\alpha 2$. This feature is seen clearly for DMe and DGlyN as seen in FIGS.

3A-B, and is also applicable to the other compounds encompassed by Formula (I). Thus, it is primarily the Ki$\alpha$1/$\alpha$2 that is affected by the modification of the third digitoxose. The Ki values of several derivatives in Table 2 (e.g. DEt) are significantly lower than for digoxin itself but a differential effect between the isoforms was not observed, so that the selectivity ratio was not improved. The Ki values of several other derivatives in Table 2 (e.g. DEtDA) are significantly lower than for digoxin itself and some differential effect was observed. In other cases (e.g DOH and DSer the Ki values were higher than for digoxin and the selectivity for $\alpha$2 was not improved. The result in Table 2 that the glycine derivative of bis-digitoxose digoxigenin (DbisGly) shows lower selectivity for $\alpha$2 over $\alpha$1 compared to the glycine derivative of the tri-digitoxose (DGly) shows that modification of the third digitoxose residues is optimal for this effect, consistent with a similar conclusion in (6). In summary, the strategy of modifying the third digitoxose moiety produced compounds with an improved ratio Ki$\alpha$1/$\alpha$2, reaching over twice the value of digoxin in the case of the most $\alpha$2-selective derivatives, DGlyN and DMe.

TABLE 2

Ki values for inhibition of Na,K-ATPase activity of isoforms $\alpha$1$\beta$1 and $\alpha$2$\beta$1 with selectivity ratios

| CG | Ki ± S.E. | | | Selectivity ratio | |
| --- | --- | --- | --- | --- | --- |
| | $\alpha$1 | $\alpha$2 | p value, n $\alpha$2 to $\alpha$1 | Ki $\alpha$1/$\alpha$2 ± S.E. | p value relative to digoxin |
| Ouabain | 97 ± 4.3 | 90 ± 14 | | 1.08 ± 0.17 | |
| Digoxigenin | 139 ± 17 | 130 ± 13.5 | | 1.07 ± 0.17 | — |
| Digoxin | 189 ± 11 | 55 ± 4.4 | 0.0001, 12 | 3.44 ± 0.34 | |
| DGlyN (1) | 152 ± 5.5 | 20.4 ± 1 | 0.0001, 8 | 7.45 ± 0.46 | 0.0001 |
| DMe (2) | 101 ± 4.4 | 15.6 ± 2.3 | 0.0001, 8 | 6.47 ± 0.71 | 0.0001 |
| DPrN (3) | 249 ± 37 | 47 ± 7.8 | 0.006, 3 | 5.28 ± 0.75 | 0.0254 |
| DSCar (4) | 102 ± 23 | 20 ± 3.6 | 0.014, 4 | 4.98 ± 1.2 | 0.029 |
| Dgly (5) | 124 ± 8.6 | 25 ± 3.9 | 0.0003, 6 | 5.10 ± 0.54 | 0.0167 |
| DOH (6) | 311 ± 18.5 | 134 ± 35 | 0.046, 3 | 2.32 ± 0.62 | — |
| DGlMe (7) | 540 ± 102 | 128 ± 11 | 0.052, 3 | 4.22 ± 0.88 | — |
| DAlaN (8) | 232 ± 28 | 67 ± 8.1 | 0.005, 3 | 3.46 ± 0.59 | — |
| DSer (9) | 316 ± 109 | 145 ± 28.5 | 0.269, 3 | 2.18 ± 0.86 | — |
| DSerN (10) | 242 ± 15 | 144 ± 3.5 | 0.033, 3 | 1.68 ± 0.13 | — |
| DEtDA (11) | 69 ± 10 | 16.7 ± 2.1 | 0.003, 4 | 4.10 ± 0.82 | — |
| DEt (12) | 53 ± 3.4 | 18.5 ± 4.9 | 0.0045, 5 | 2.88 ± 0.78 | — |
| DMeCF$_3$ (15) | 199 ± 33 | 44 ± 7 | 0.01, 3 | 4.50 ± 1.0 | — |
| DbisGly (16) | 80 ± 5.5 | 34.9 ± 12 | 0.075, 3 | 2.29 ± 0.80 | — |
| Dbis* (20) | 196 ± 8.5 | 74 ± 5 | 0.006, 3 | 2.65 ± 0.81 | — |

*Dbis is digoxigenin bis digitoxide.

The CG abbreviation corresponds to the following starting amine: DOH-hydroxylamine; DGly-glycine; DGlMe-glycine methyl ester; DGlyN-glycinamide; DAlaN-alaninamide; Dser-serine; DSerN-serinamide; DSCar-semicarbazide; DPrN-proprionamide; DEtDA-ethylene diamine; DMe-methylamine; DEt-ethylamine; DMeCF$_3$-2,2,2-trifluoroethylamine; DbisGly-bis-digitoxoside glycine, p values were calculated by the t-test and denoted as *p<0.05, P<0.01, *p<0.001. n, number of independent experiments, p ($\alpha$2val) indicates the significance of differences between Ki$\alpha$2$\beta$1 and Ki$\alpha$1$\beta$1. p (v digoxin) indicates the significance of the difference of the selectivity ratio (Ki$\alpha$1$\beta$1/Ki$\alpha$2$\beta$1) compared to the (Ki$\alpha$1$\beta$1/Ki$\alpha$2$\beta$1) of digoxin.

Figure 4:
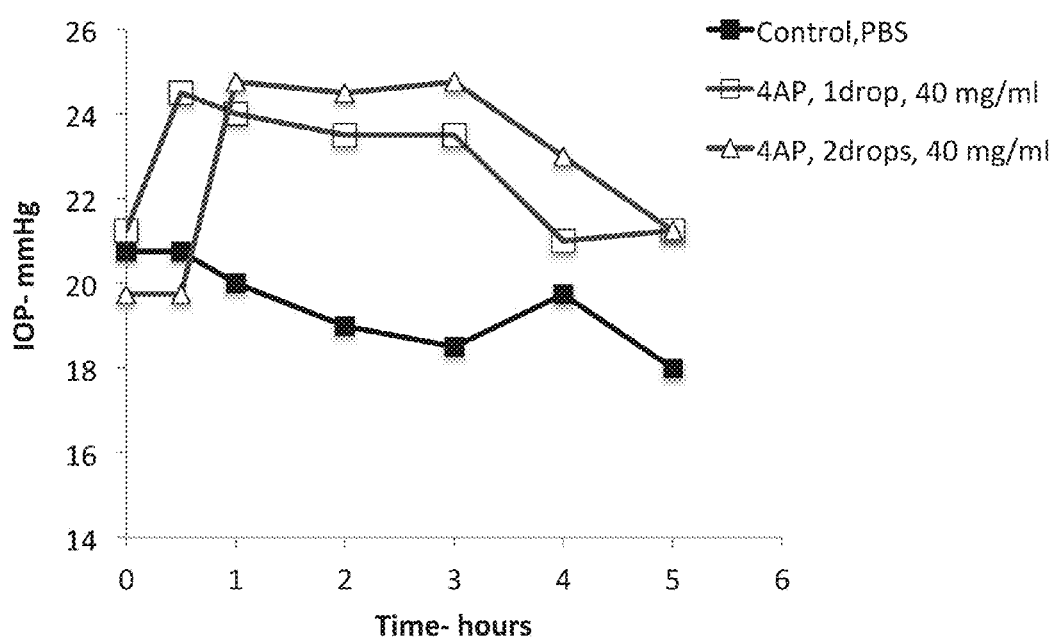
FIG. 4 4-aminopyridine (4AP)-induced transient ocular hypertension in rabbits. Control ■; 4AP, 1 drop (40 mg/ml) □; 4AP, 2 drops (40 mg/ml) Δ.

Example 3: Reduction of Intra-Ocular Pressure by Topically Applied Digoxin and Perhydro-1,4-Oxazepine Derivatives Intra-ocular pressure in rabbits was measured using of a "Reichert Model 30™ Pneumatonometer" after anesthetizing the cornea with local anesthetic. Two different pharmacological agents were used to induce acute elevation of IPO and determine whether topically applied glycosides of the present invention are able to counter such an effect. First, IOP elevation was induced acutely with 4-aminopyridine (4AP), which has been previously reported to acutely and transiently raise IOP in rabbits eyes by 4-8 mm Hg from a resting IOP of 22-24 mmHg (16). The mechanism of ocular hypertension induced by 4AP, which is a well-known blocker of a voltage-dependent K channel, was shown to involve release of norepinephrine from sympathetic nerves of the iris-ciliary body, leading to an increased rate of aqueous humour inflow. FIG. 4 confirms the basic effect of 4AP. One or two drops of 4AP in each eye raised the IOP by 3-6 mm Hg, and the effect was dissipated after 5 hours.

Figure 5A:
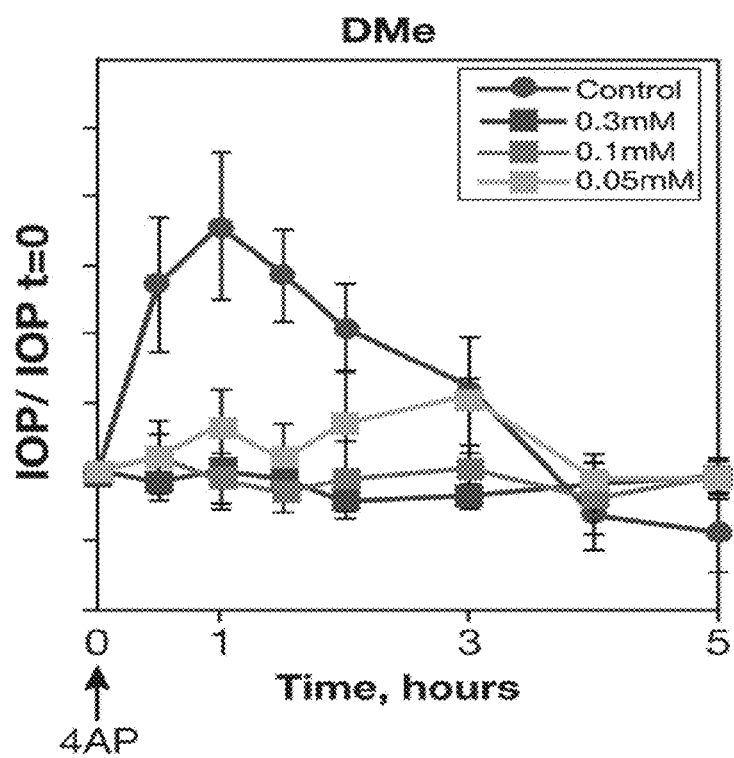
FIGS. 5A-E Effects of DMe (FIG. 5A), DGlyN (FIG. 5B), digoxin (FIG. 5C), ouabain (FIG. 5D) and digoxigenin (FIG. 5E) on 4AP-induced ocular hypertension. Cardiac glycosides (CG's) (1 drop, 25 μl) at the indicated concentrations were added to both eyes 30 min before addition of 4AP (40 mg/ml, 1 drop, 25 μl). During this pre-incubation period there was little or no change in IOP. IOP was measured at the indicated times after addition of 4AP. In each experiment one rabbit was used for each concentration. The values are the mean of the IOP in both eyes.
Figure 5B:
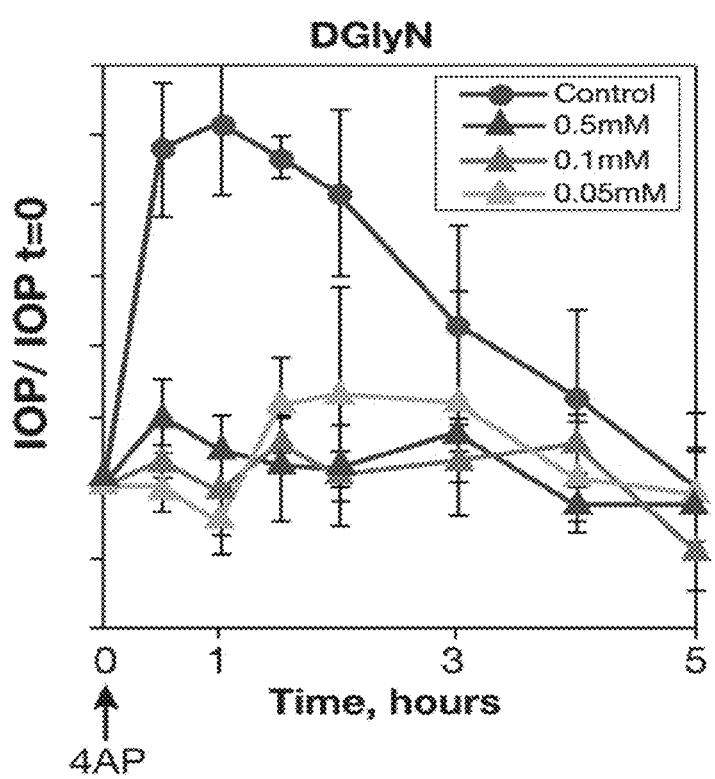
Figure 5C:
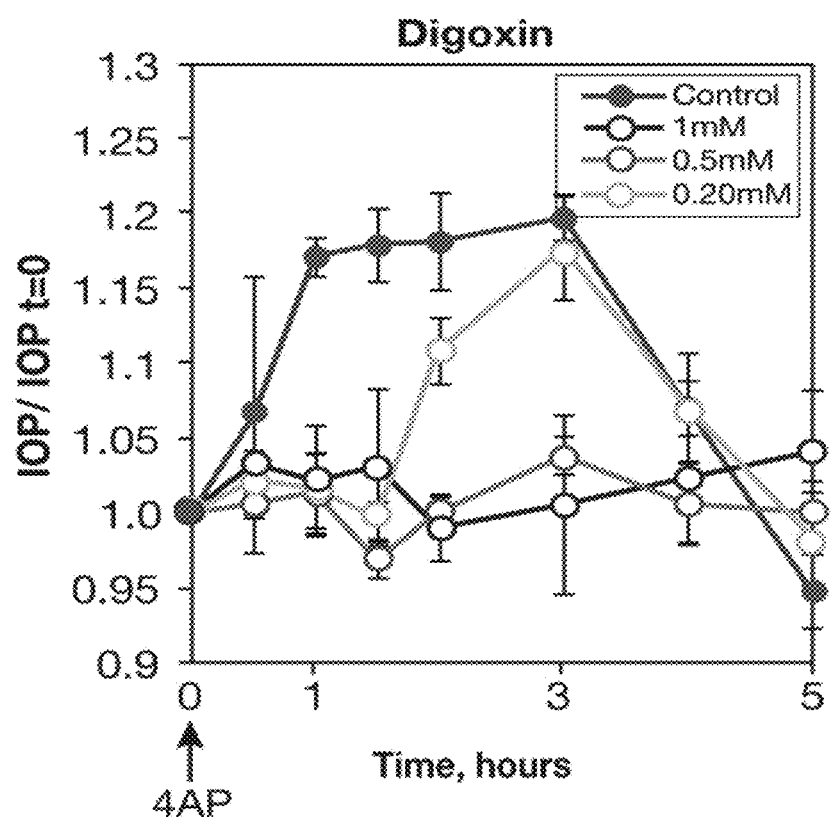
Figure 5D:
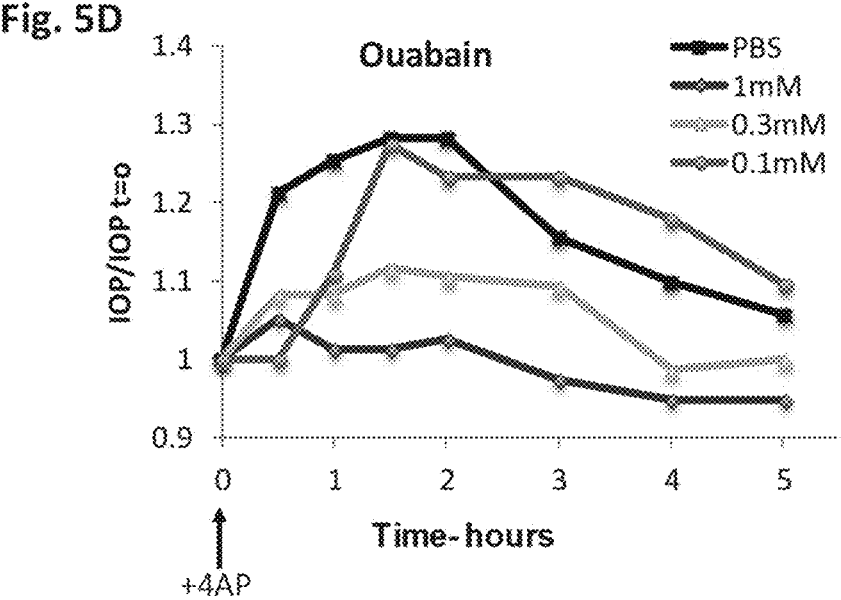
Figure 5E:
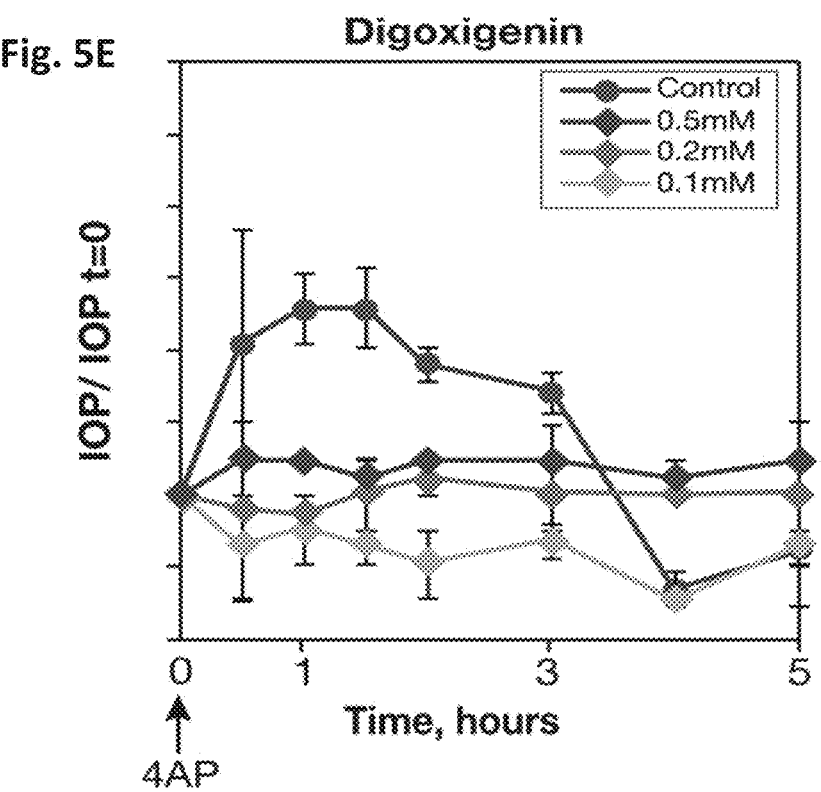

Since the IOP reflects a balance of the inflow and outflow of aqueous humour, reduction of the increased 4AP-induced inflow of aqueous humour by cardiac glycosides should prevent the increase in IOP. Thus, the standard experimental design to test effects of cardiac glycosides involved topical application of the compounds (1 drop in each eye) 30 minutes prior to application of 4AP and measurement of IOP every 30 minutes over five hours. FIGS. 5A-PE show effects of DMe (FIG. 5A), DGlyN (FIG. 5B). digoxin (FIG. 5C), ouabain (FIG. 5D) and digoxigenin (FIG. 5E) on IOP using this protocol. Each experiment was done three times, but the figures depict a representative experiment using a different rabbit for each concentration of the cardiac glycoside. The plotted values represent the average pressures for both eyes although the values are similar in each eye measured separately. Digoxin (FIG. 5C) at a high concentration (1 mM) is able to prevent the 4AP-induced rise in IOP, while 0.25 mM digoxin is poorly effective. By comparison, both DMe and DGlyN (FIG. 5A and FIG. 5B respectively), the most $\alpha$2-selective of the new perhydro-1,4-oxazepine derivatives, are effective at much lower concentrations (0.05-0.1 mM) than digoxin. Similarly the aglycone of digoxin, digoxigenin, effectively reduced IOP at lower concentrations than digoxin (FIG. 5E). Finally, ouabain, a widely used water-soluble cardiac glycoside, somewhat reduced IOP only at 1 mM while lower concentrations were poorly effective (FIG. 5D).

Figure 6:
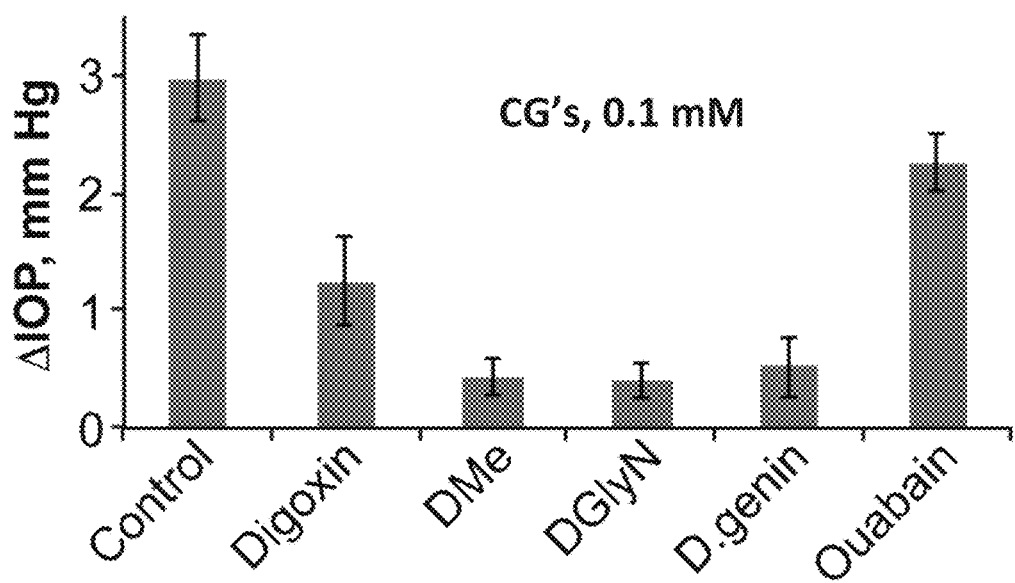
FIG. 6 Comparison of the change in IOP with different CG's.

FIG. 6 compares the relative effects of DGlyN, DMe, digoxigenin, digoxin and ouabain, on IOP all at 0.1 mM and one time point. The data represent the average effect ±SEM of the three separate experiments (i.e. 6 eyes in all) and confirm the order as DGlyN≈DMe≈digoxigenin>digoxin>ouabain.

Figure 7A:
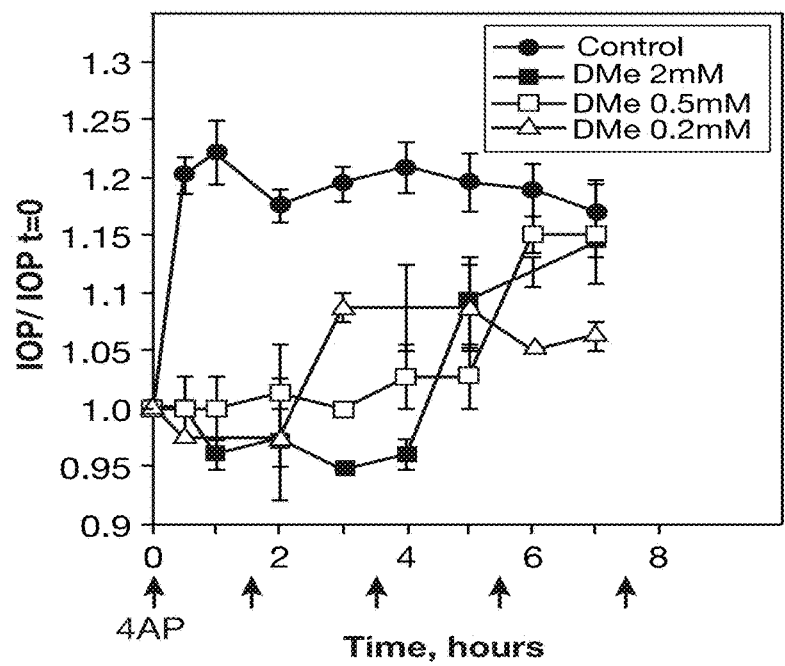
FIGS. 7A-C Time-course of effects of digoxin derivatives on IOP. In this experiment the IOP was elevated for 7-8 hours, by application of 4AP every 2 hours either in the absence of cardiac glycosides or after application of one drop of the cardiac glycoside (FIG. 7A and FIG. 7B), or one drop of cardiac glycoside was applied one hour after the first application of 4AP (FIG. 7C). All the other conditions and measurements are as described in FIGS. 5A-E.
Figure 7B:
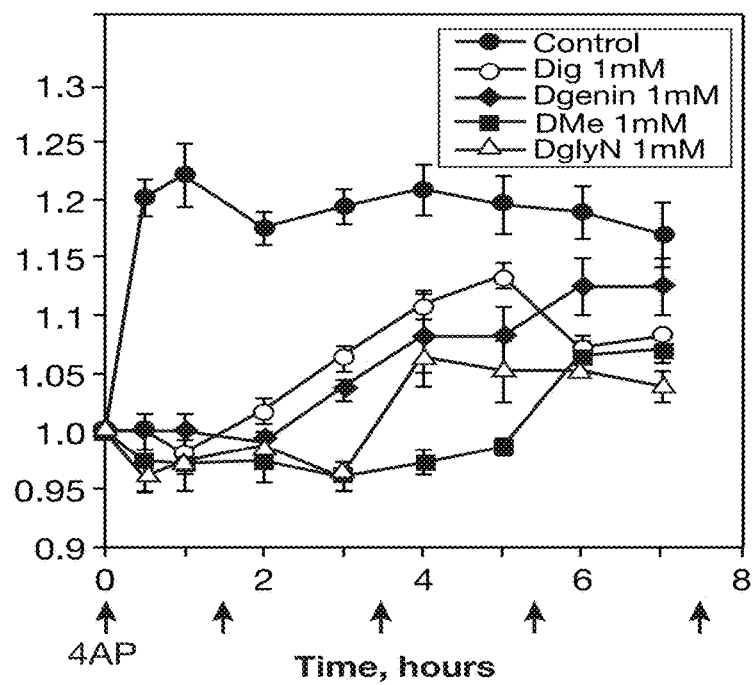
Figure 7C:
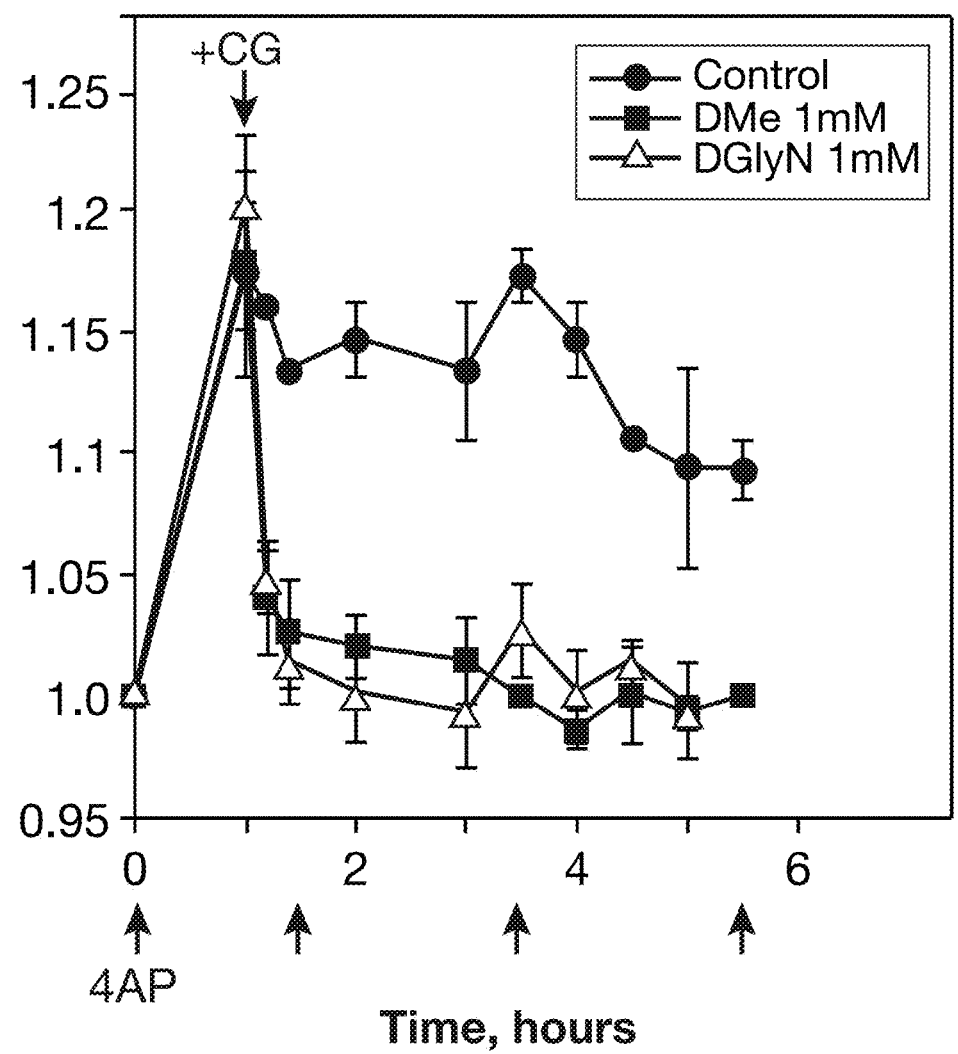

Over time, the cardiac glycosides that penetrate to the ciliary epithelium after a single application will be washed out of the eye into the general circulation and so the effect on IOP will dissipate. Although FIGS. 5A-E and 6 demonstrate that the cardiac glycosides reduce IOP with greater or less efficacy, by this experimental protocol the longevity of the effect cannot be evaluated due to the transient nature of the 4AP effect itself. Thus, additional experiments were conducted in which the effect of a single drop of digoxin, digoxigenin, DGlyN, DMe or ouabain was compared when 4AP was then added every two hours so as to maintain the IOP at the elevated level for 7-8 hours, even in the absence of the cardiac glycosides (FIGS. 7A-C). By this protocol, the reduction of IOP is indeed seen to be transient in FIGS. 7A-C. FIG. 7A shows a representative experiment with DMe that demonstrates a clear dependence of the wash-out time on concentration. IOP is held at the low level for 5.8, 4.5 and 2.5 hours for 2 mM, 0.5 mM and 0.2 mM respectively, before the IOP rises back to the elevated level with 4AP. Other experiments showed that at equal concentrations the wash-out time for DGlyN is slightly faster than for DMe. Notable differences in wash-out times were detected between DMe, DGlyN, digoxigenin, digoxin and ouabain when they were applied at equal concentrations (1 mM). As seen in FIG. 7B, DMe maintained IOP at the low level for about 5.5 hours, by comparison with 3.5 hours for DGlyN, about 2 hours for digoxigenin and only 1 hour for digoxin. Ouabain is washed out at a rate between that of digoxin and digoxigenin. The data is not shown for clarity. In short, the most $\alpha 2$-selective derivatives DMe (compound 2) and DGlyN (compound 1) produce the longest acting effect to reduce IOP, compared to either digoxin (a less $\alpha 2$-selective cardio-glycoside (CG)), or digoxigenin a non-selective CG.

FIG. 7C shows that DGlyN and DMe rapidly reverse pre-established ocular hypertension. DGlyN or DMe (0.1 or 1 mM) were applied one hour after the first application of 4AP, which was added every two hours. Evidently, within 30 minutes DGlyN and DMe reversed the initial rise in IOP, indicating that the compounds permeate the cornea and bind to the pump sufficiently fast to have this effect. The normalized IOP was then maintained for at least 4 hours, as in FIG. 7B. Independently of the superior effects of $\alpha 2$-selective derivatives at low concentrations compared to digoxin itself, the rapid onset of the effects of DGlyN and DMe is suggestive of inhibition of $\alpha 2$, because $\alpha 2$ is known to bind cardiac glycosides much more rapidly than $\alpha 1$ (17).

Figure 8A:
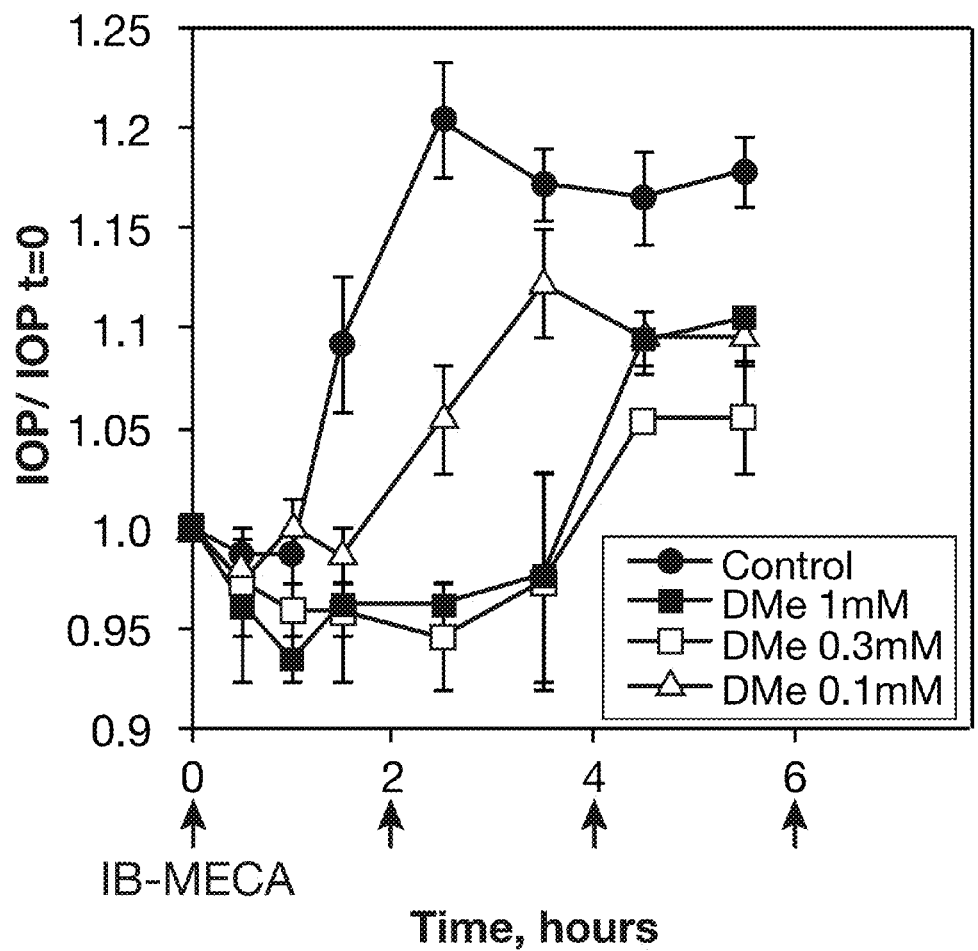
FIGS. 8A-C Effect of DMe, DGlyN and digoxigenin on IB-MECA-induced ocular hypertension.
Figure 8B:
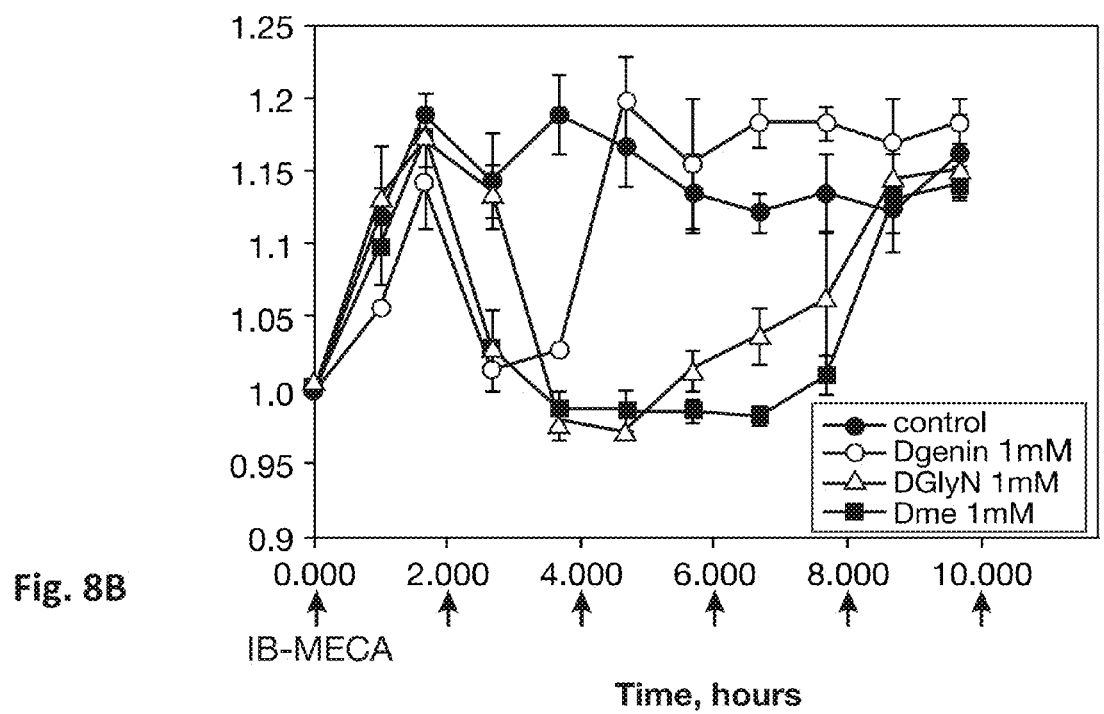
Figure 8C:
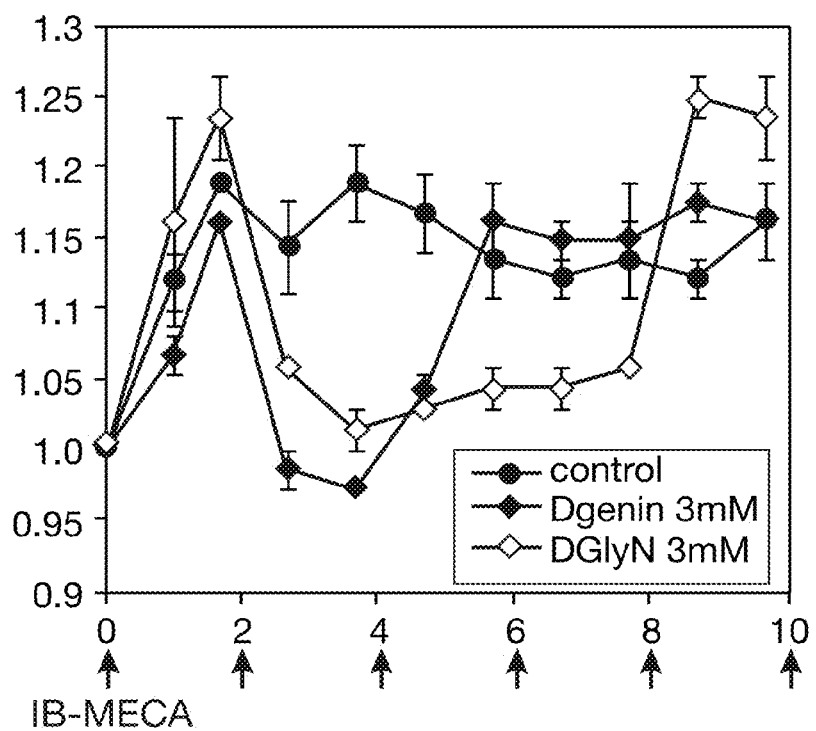

To verify that digoxin derivatives inhibits aqueous humour inflow directly and not act indirectly by, for example, interfering with the 4AP itself, topical IB-MECA was used. IB-MECA induces acute ocular hypertension by a different and well-defined mechanism. Namely, IB-MECA is a selective agonist of the A3-adenosine receptor, and rises aqueous humour inflow and IOP by activating Cl channels of the NPE cells (18, 19). A single drop of IB-MECA (1 µM) induced a significant but transient increase in IOP, while repeated application each 2 hours maintained increased IOP over 4-5 hours (see FIG. 8A Control). FIG. 8A depicts the effects of DMe (0.1-1 mM) applied prior to the IB-MECA, and a similar result was obtained for DGlyN (not shown). FIG. 8B depicts effects of digoxigenin, DGlyN and DMe (1 mM) applied after the IB-MECA. The effects of digoxigenin, DGlyN and DMe at 1 mM were almost the same as seen with 4AP in FIG. 7C, obviously excluding the notion that CG's interfere with the action of 4AP itself. In addition, the duration of the effect was significantly greater for DMe and DGlyN than for digoxigenin. Furthermore, when the concentration of DGlyN and digoxigenin was raised to 3 mM, the difference in duration of the effect was greatly amplified compared to the experiment with 1 mM (see FIG. 8C).

Corneal thickness was also measured after application of Digoxin (1 mM), DGlyN (0.5 mM), DMe (0.5 mM) and ouabain (1 mM) after 4AP. At least over a time scale of 4 hours, the corneal thickness, measured in microns, was not significantly affected. Thus, in this study, no change in corneal thickness was detected (Table 3), indicative of lack of local toxic effects. In addition neither redness nor local irritation were observed in the conjunctiva or cornea. Similar results were obtained with CG's applied after IB-MECA.

TABLE 3

Pachymetry-Corneal thickness before and after application of cardiac glycosides

| Time | Digoxin 1 mM | | DGlyN 0.5 mM | | DMe 0.5 mM | | Ouabain 1 mM | |
|------|------|------|------|------|------|------|------|------|
|      | RE   | LE   | RE   | LE   | RE   | LE   | RE   | LE   |
| 0 h  | 462  | 470  | 496  | 498  | 507  | 465  | 461  | 455  |
| 2 h  | 422  | 450  | 476  | 462  | 476  | 440  | 405  | 409  |
| 4 h  | 451  | 467  | 454  | 455  | 498  | 453  | 414  | 422  |

RE, right eye
LE, left eye.
Corneal thickness is given in microns.
Each value represents the average of three independent measurements.

Example 4: Dissociation of Cardiac Glycosides from $\alpha 2\beta 1$

Figure 9:
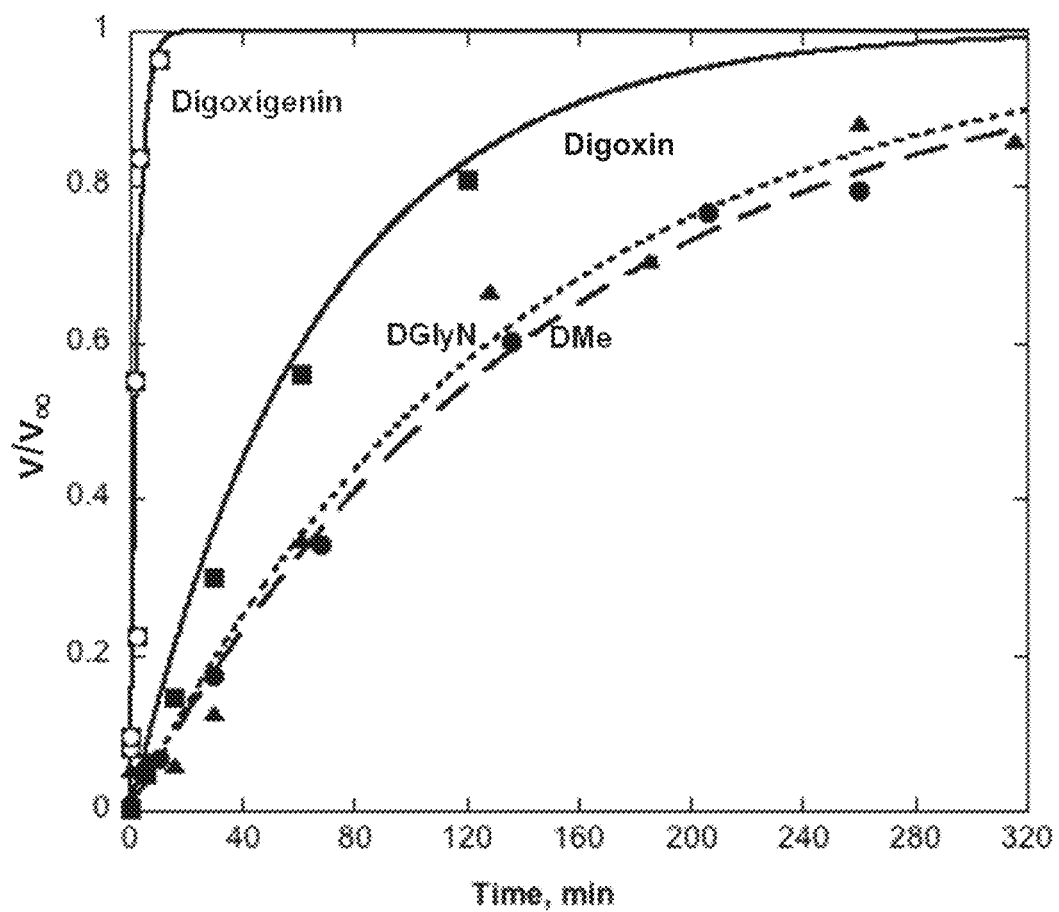
FIG. 9 Dissociation of digoxigenin, digoxin, DGlyN and DMe from the α2 isoform.

Since the principal isoform in NPE cells is $\alpha 2$ and dissociation from the pump is expected to affect the duration of the effects on IOP, the dissociation rates of different cardiac glycosides from the purified $\alpha 2\beta 1$ isoform were compared. The dissociation rates of digoxin, digoxigenin, DGlyN and DMe were compared using the protocol described in (20). FIG. 9 depicts representative experiments for each of the four compounds and Table 4 shows the average rate-constants and half-times from three or four experiments. Evidently, the aglycone digoxigenin dissociates much faster than digoxin or any other glycone, and DMe and DGlyN also dissociate significantly slower than digoxin itself. The slow dissociation of DMe and DGlyN suggest their potential of a durable effect on IOP.

TABLE 4

Rates of dissociation of cardiac glycosides from the $\alpha 2\beta 1$ isoform complex.

| CG | k ± SEM min$^{-1}$, n | t$_{1/2}$ ± SEM min | p vs. digoxin |
|----|------|------|------|
| Digoxigenin | 0.645 ± 0.189, 3 | 1.07 ± 0.23 | 0.0006 |
| Digoxin | 0.015 ± 0.001, 4 | 47.5 ± 5.05 | |

TABLE 4-continued

Rates of dissociation of cardiac glycosides
from the α2β1 isoform complex.

| CG | k ± SEM min$^{-1}$, n | t$_{1/2}$ ± SEM min | p vs. digoxin |
|---|---|---|---|
| DGlyN | 0.009 ± 0.001, 3 | 78.8 ± 8.73 | 0.02 |
| DMe | 0.0067 ± 0.004, 3 | 103 ± 6.12 | 0.001 |

Example 5: Digoxin Derivatives with Enhanced Selectivity for the α2β3 Complex

Because α2β3 and not α2β1 is the major isoform complex in NPE cells, it was further investigated whether the β1, β2, or β3 isoform is an important factor.

Molecular Modeling of the Digoxin Bound Na,K-ATPase

Figure 10A:
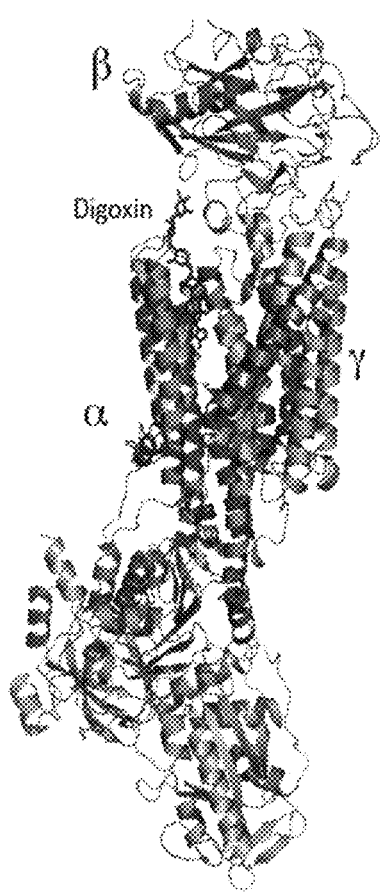
FIGS. 10A-D Model of Digoxin bound to the Na,K-ATPase.
Figure 10B:
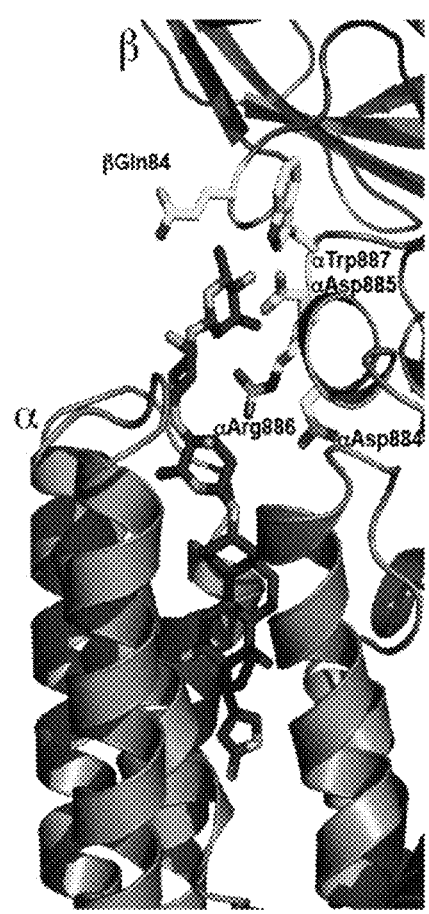

A molecular insight to the interactions of the third digitoxose residue and isoform selectivity is illustrated in FIG. 10A. The figure presents a molecular model in which the digoxin molecule (co-ordinates 3B0W) was introduced onto the high affinity ouabain bound molecule (4HYT) (14) so that the lactone and steroid portions of ouabain and digoxin overlap closely, and then a minimal energy structure was obtained. The three digitoxose residues point outwards towards both α and β subunits. The enlarged image in FIG. 10B shows the digitoxose moiety in proximity (<3.5 A) to residues AspAspArgTrp887 in L7/8 of α, the third digitoxose being close to both αTrp887 and also βGln84. Support for this orientation towards the β subunit comes from an old observation that photoaffinity probes located in the third digitoxose of digitoxin label both α and β subunits, whereas photoaffinity probes located in other regions of cardiac glycoside molecules label only the α subunit (21, 22). As suggested by the model, αTrp887 is one of only four residues in extracellular loops that are different in α2 (and α3) from α1, (Gln119, Glu307, Val 881 and Trp887 in pig α1), and were inferred previously to be candidates for determining isoform selectivity (23) Close proximity to one of these four residues fits very well with the notion that interactions of the third digitoxose are important for isoform selectivity, and the present findings that derivatives of the third digitoxose can enhance isoform selectivity. In α2, Trp887 is replaced by a threonine.

Figure 10C:
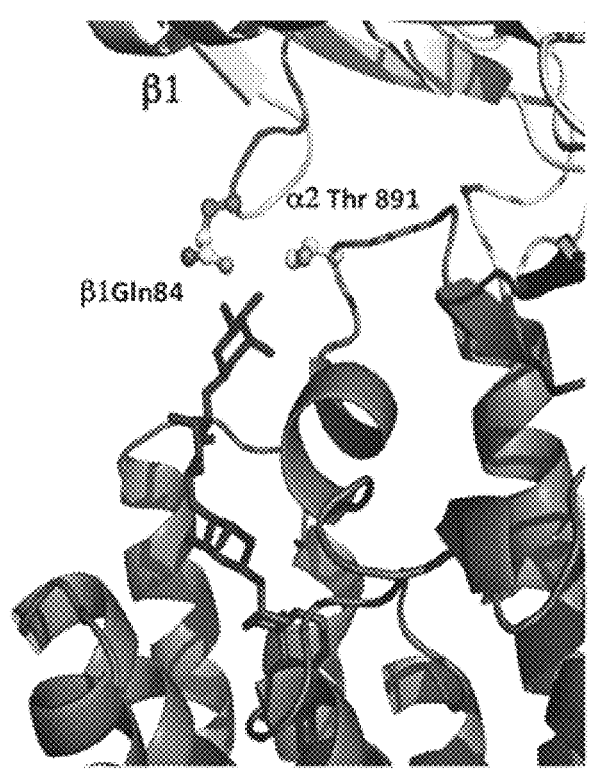
Figure 10D:
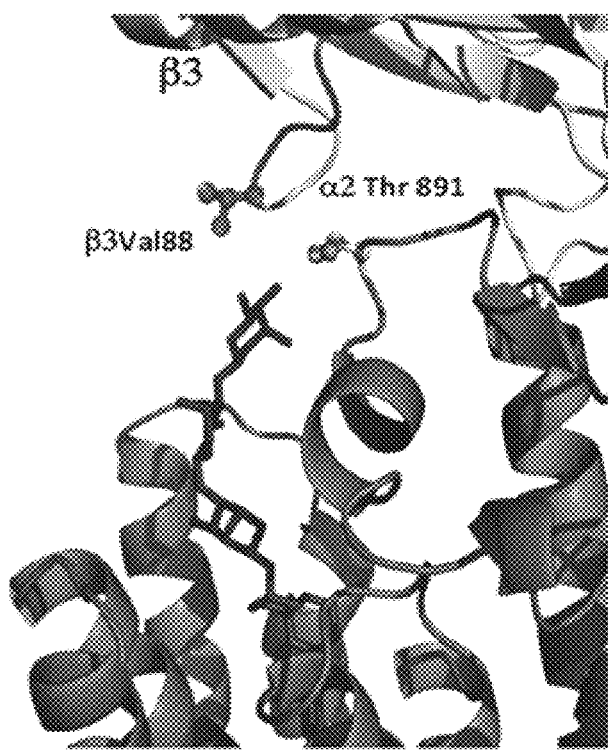

In addition, Gln84 in β1 is replaced by Val89 in β3 and Glu in β2 (FIGS. 10C and D). Since α2β3 is the major isoform complex in NPE cells it seemed that by introducing larger aliphatic groups into the perhydro-1,4-oxazepine digoxin derivatives than Me and Et which were already tried, it might be possible to produce digoxin derivatives with enhanced selectivity for α2β3 compared to α1β1 the major isoform complex in all other cells. Another possible advantage of more hydrophobic derivatives is that they could be expected to be more permeate through the cornea and thus, potentially, effective in IOP reduction at lower concentrations than DMe or DGlyN.

Expression, Purification and Characterization of Human α2B3 and α2β2 Isoform Complexes.

Figure 11:
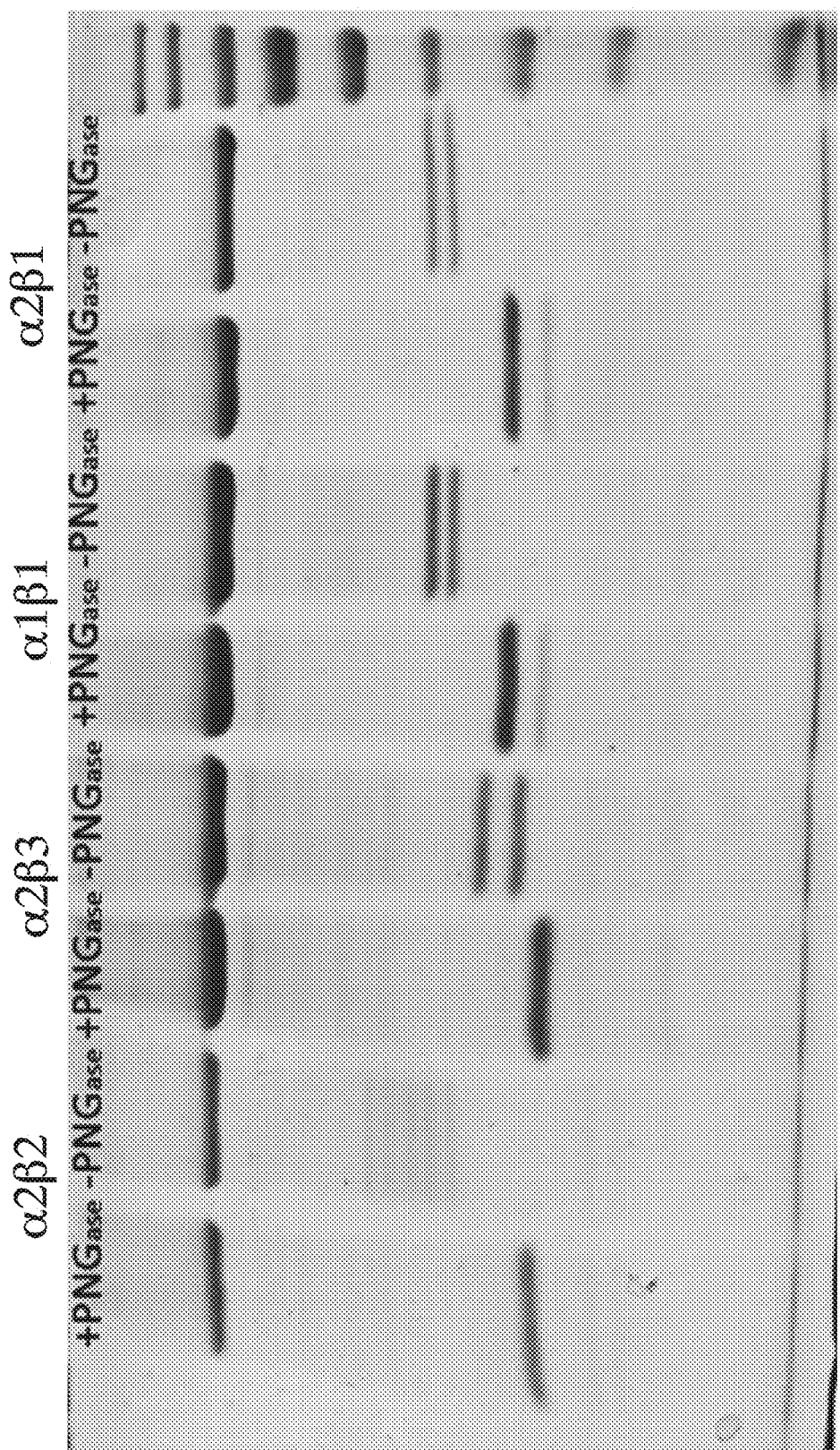
FIG. 11 shows the expression of α2β3 and α2β2 as well as α2β1 and α1β1 isoform complexes in Coomassie blue stained gels. The proteins were denatured prior to treatment with PNGase.
Figure 12:
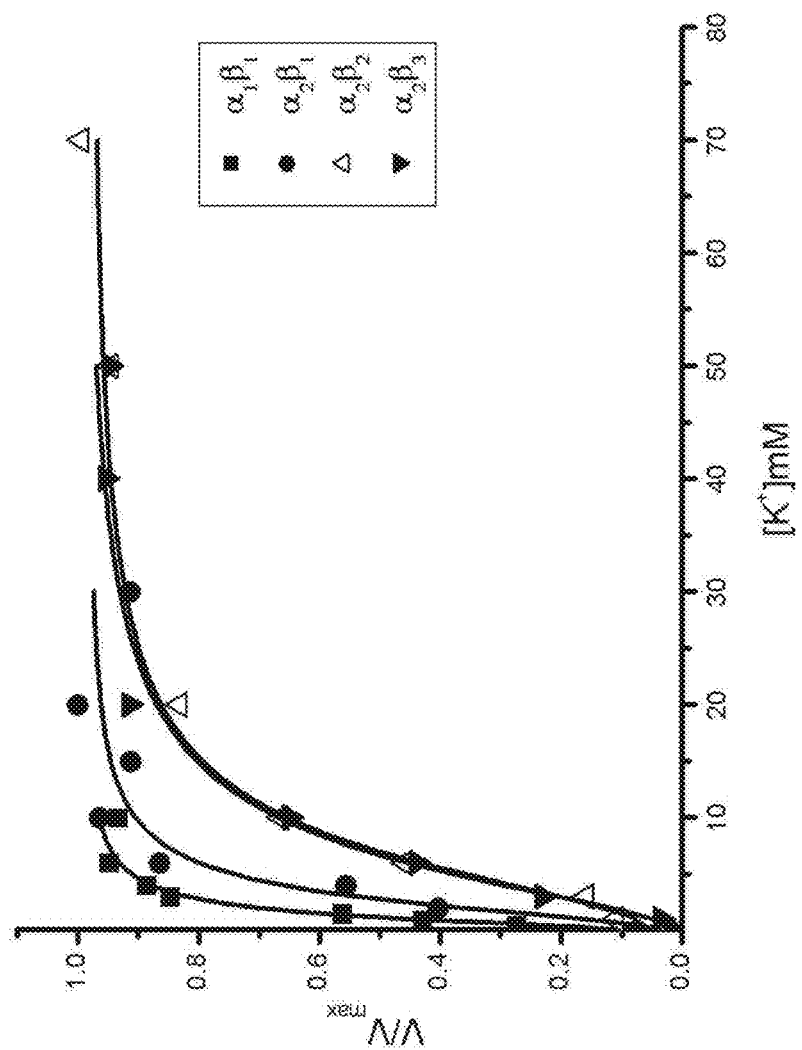
FIG. 12 K-activation of Na,K-ATPase activity of α1β1, α2β1, α2β2, α2β3 isoform complexes.
Figure 13:
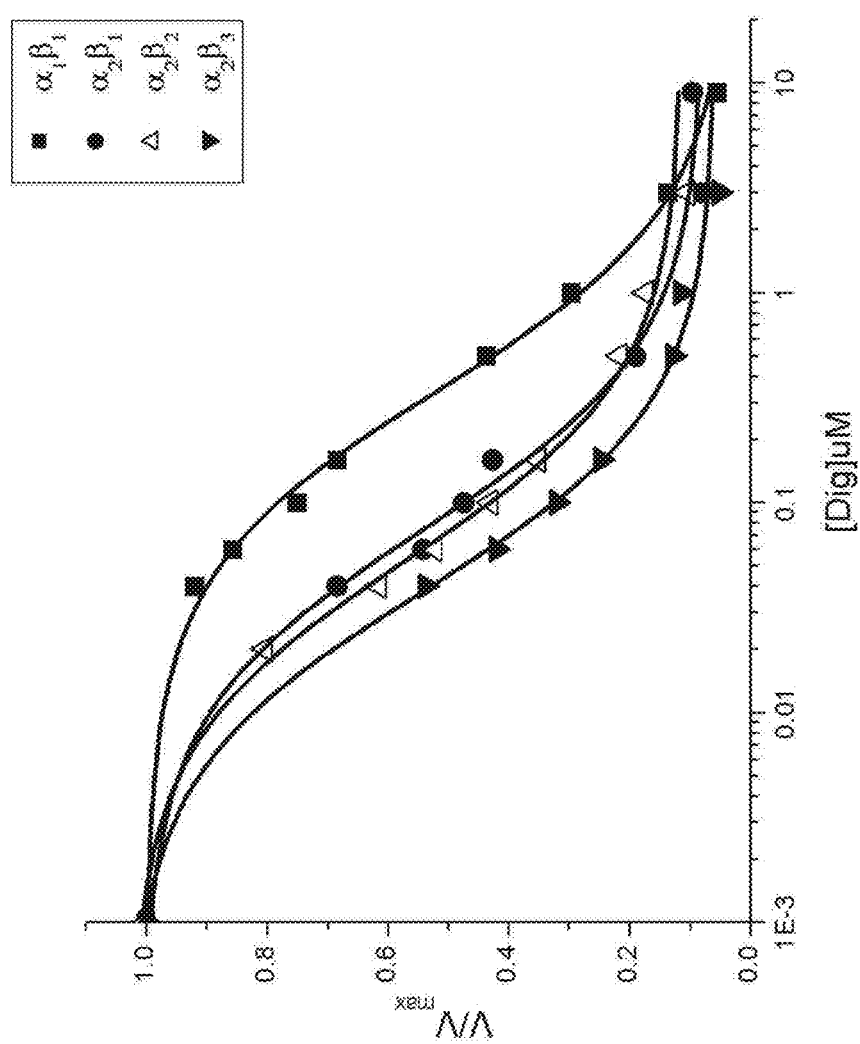
FIG. 13 Inhibition of the Na,K-ATPase activity of α1β1, α2β1, α2β2, α2β3 by digoxin.

To develop compounds with higher selectivity to α2β3 human, α2β3 and α2β2 human isoform complexes were expressed as described in the Methods below. FIG. 11 shows a protein gel of the purified isoform complexes α2β1, α2β2, α2β3 and α1β1 before or after treatment with PNGase (in the denatured state), β1 has 3 glycosylation sites, β3 has two glycosylation sites while β2 has seven glycosylation sites. The mobility order on the gel, β3>β2>β1, fits well the predicted masses of the deglycosylated subunits of β1, 37172.6>β2, 35422.2>β3, 33678.9. The average Na,K-ATPase activities of the purified complexes were; α1β1, 19.3±2; α2β1, 18.2±1.6; α2β2, 7.7±1.8 and α2β3 9.7±0.26 µmoles/min/mg protein (n=4). Because cardiac glycosides and K ions are mutually antagonistic, an important point in relation to cardiac glycosides binding is the K0.5 K for activation of Na,K-ATPase. The term "$K_{0.5}$ K" as used herein means the half maximal concentration of potassium ions (K) required for activation of Na,K-ATPase activity. FIG. 12 and Table 5 shows that the apparent affinities for K are significantly different between the isoform complexes, in the order α1β1<α2β1<α2β2<α2β3. Inhibition by digoxin is more effective for the isoforms with higher $K_{0.5}$ K (Ki α1β1>α2β1>α2β2>α2β3), hence leading to a higher selectivity for α2β3 over α1β1 (FIG. 13). This increased selectivity is explained by a lower degree of K-digoxin antagonism and is expected for all the cardiac glycosides to the same extent as for digoxin.

TABLE 5

$K_{0.5}$ K for activation of Na,K-ATPase activity of α1β1, α2β1, α2β2 and α2β3 isoform complexes

| α1β1 $K_{0.5}$K-mM ± SEM | α2β1 $K_{0.5}$K-mM ± SEM | α2β2 $K_{0.5}$ K-mM ± SEM | α2β3 $K_{0.5}$ K-mM ± SEM |
|---|---|---|---|
| 1.25 ± 0.03 n = 4 | 2.72 ± 0.14 n = 6 | 7.3 ± 0.19 n = 6 | 6.4 ± 0.5 n = 5 |

Synthesis and Isoform Selectivity of Aliphatic Derivatives of Digoxin.

Figure 14:
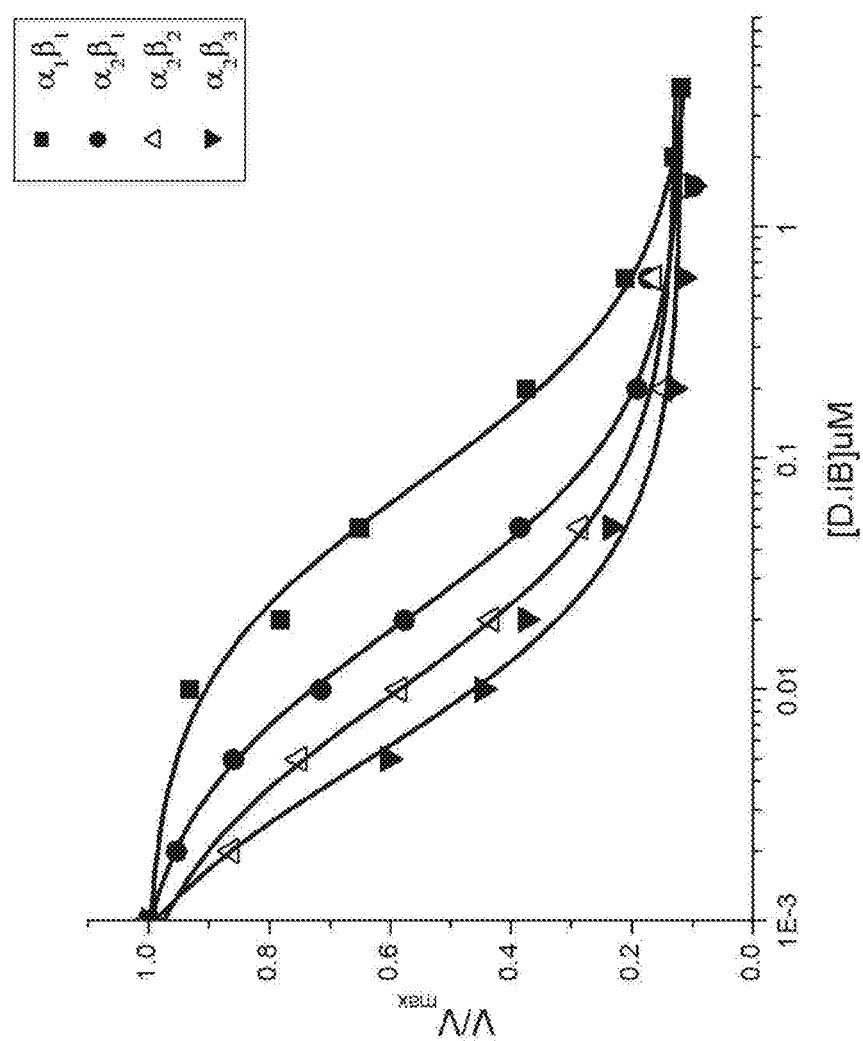
FIG. 14 Inhibition of the Na,K-ATPase activity of α1β1, α2β1, α2β2, α2β3 by DIB.

Additional set of perhydro-1,4-oxazepine digoxin derivatives with aliphatic substituents propyl (DP), iso-propyl (DIP), iso-butyl (DIB), tert-butyl (DtB) and trifluoroethyl (DMeCF3) has been synthesized and purified. Table 6 shows results of inhibition and selectivity of the most recent aliphatic derivatives for four Na,K-ATPase isoform complexes, in comparison to digoxin itself and DMe, FIG. 14 illustrates the effects of the most selective isobutyl derivative, DIB. No significant difference was observed in α1β1 versus α2β1 when compared to DMe. However, for α2β3, all of the aliphatic derivatives including DMe are significantly superior to digoxin and in the case of the isobutyl derivative the selectivity ratio reaches 16-fold. Generally, the curves for α2β2 lie between those for β2β3 and α2β1. As mentioned above, the difference in $K_{0.5}$K between the α2β1-3 complexes should translate into a difference in Ki as seen for digoxin in the sense Ki α2β1>α2β2≥α2β3. However, the increase in selectivity for α2β3:α1β1 is significantly higher than seen with digoxin (6.2-fold) for all these new derivatives and especially so for the isobutyl derivative, DIB (16-fold). This finding could imply that all the aliphatic derivatives, but especially DIB, interact more specifically with α2β3 than with α2β1. In any event the Ki of 5.8 nM for inhibition of α2β3 by DIB is lower than seen for any of the other aliphatic (or other) derivatives.

Figure 15:
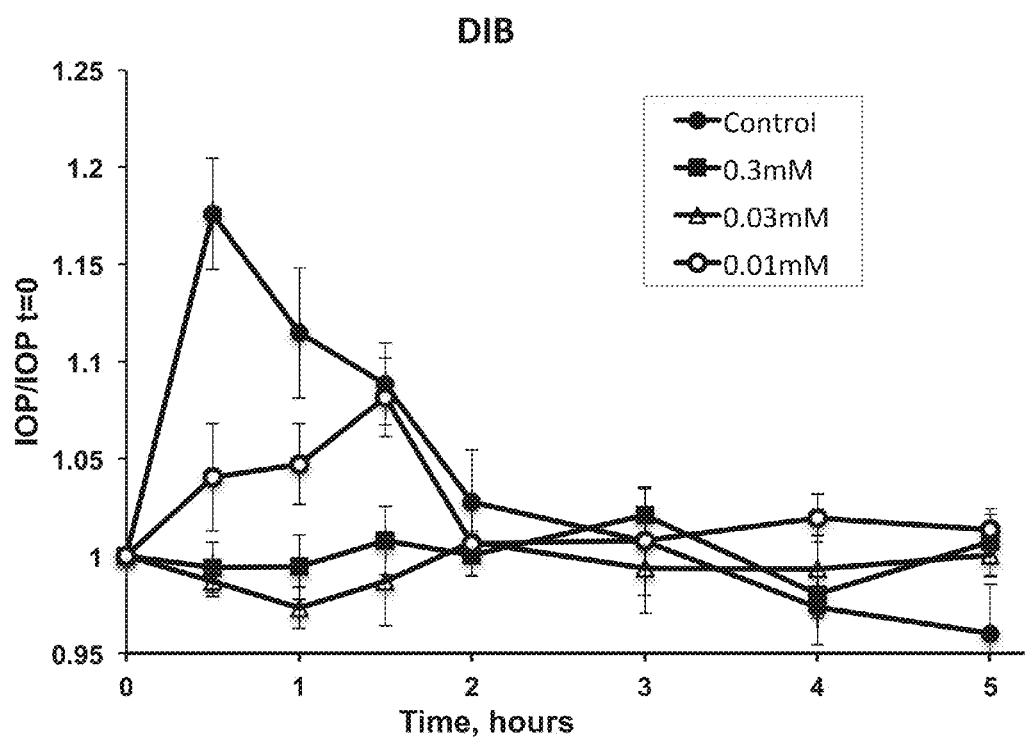
FIG. 15 Inhibition of acute ocular hypertension by DIB.

The low Ki for inhibition of α2β3 implies that DIB could be a good inhibitor of IOP in rabbits. This was tested in experiments summarized in FIG. 15. Indeed DIB applied topically prior to 4AP effectively prevented the rise in IOP. The concentration required to fully prevent the rise in IOP (>30 µM) was about 2-fold lower than required for the most effective derivative previously tested (DMe).

TABLE 6

Selectivity of aliphatic digoxin perhydro-1,4-oxazepine derivatives for the α2β3 isoform complex

| CG | Ki, nM ± SEM | | | | Selectivity | | | n |
|---|---|---|---|---|---|---|---|---|
| | α1β1 | α2β1 | α2β2 | α2β3 | α1β1/α2/β1 | α1β1/α2/β2 | α1β1/α2β3 | |
| Digoxin | 268 ± 13.8 | 58.7 ± 5.4 | 58 ± 1.9 | 42.8 ± 3.0 | 4.5 | 4.6 | 6.2 | 7 |
| DMe (2) | 103 ± 5.6 | 15.3 ± 1.2 | 20.36 ± 1.8 | 10.8 ± 0.6 | 6.7 | 5.07 | 9.5 | 7 |
| DEt (12) | 137.9 ± 12.6 | 23.2 ± 0.9 | 16.4 ± 1.6 | 14.4 ± 1.27 | 5.9 | 8.3 | 9.5 | 4 |
| DP (13) | 87.7 ± 7.9 | 18.3 ± 1.68 | 10.5 ± 1.8 | 9.8 ± 1.1 | 4.8 | 8.3 | 8.8 | 5 |
| DIP (21) | 149 ± 20.7 | 28.9 ± 1.7 | 16.7 ± 1.9 | 10.3 ± 1.8 | 5.1 | 8.9 | 14.4 | 4 |
| DIB (14) | 92 ± 8.9 | 20.6 ± 1.4 | 10 ± 0.8 | 5.8 ± 0.6 | 4.4 | 9 | 16 | 5 |
| DtB (22) | 135 ± 12.1 | 21.6 ± 5.6 | 18.4 ± 1.1 | 16.3 ± 0.28 | 6.2 | 7.3 | 8.2 | 4 |
| DTMS (23) | 108 | 31.5 | 15 | 7.8 | 3.4 | 7.2 | 13.8 | 2 |
| DMeCF$_3$ (15) | 119 ± 15.0 | 28.6 ± 0.9 | 18.1 ± 1.9 | 12.4 ± 1.5 | 4.1 | 6.5 | 9.6 | 3 |

In conclusion, it has now been demonstrated that modification of the third digitoxose residue of digoxin can produce derivatives with increased selectivity for α2 over α1. Compared to digoxin (Kiα1/α2 3.44-fold), the selectivity ratio was significantly increased in the order DGlyN>DMe>DGly≈DPrN≈DSCar, reaching a maximal value of Kiα1/α2=7.45 for DGlyN (Table 2).

Furthermore the selectivity ratio, Kiα2β3/α1β1, 6.2 for digoxin itself, was significantly enhanced for all the more aliphatic derivatives DP, DIP, DIB, DtB and DMeCF$_3$, reaching to c.16-fold for DIB.

Considering the structures of the substituents in the perhydro-1-4-oxazepine ring (Tables 1, 2 and 6), it seems that the increased α2:α1 selectivity (especially α2/β3) is achieved with small R-groups having H-bonding potential (e.g., glycine, glycinamide, proprionamide, semicarbazide, semithiocarbazide), or small hydrophobic groups (e.g., Me, Et, Pr, iPr and t-Bu), while larger substituents (alanine, alaninamide, serine, serinamide improve selectivity to a lower extent, although these compounds may also be therapeutically useful. Important features of isoform selectivity are (a) α2-selectivity may be restricted to digitalis glycosides with β-digitoxose residues since, for example, ouabain, an α-rhamnoside, is slightly selective for α1 over α2 and (b) the third digitoxose residue is optimal as concluded above and also in (6).

While the structures of the ouabain-bound conformations of renal Na,K-ATPase (12-14) are consistent, in general, with the observed lack of isoform selectivity of aglycones, because ouabain itself is only slightly selective for α1 over α2 (Table 2), these structures cannot explain in detail either the moderate selectivity of digoxin for α2 or increased selectivity for α1 of perhydro-1,4-oxazepine derivatives. Without wishing to be bound by any particular mechanism or theory, it is hypothesized that the relatively high selectivity of the perhydro-1,4-oxazepine derivatives of the invention (e.g., DGlyN) for α1 over α1, indicates a differential interaction with the isoform-specific residues in the exterior loops of α1 and α1. The very large difference of dissociation rates between aglycones and glycones emphasize the role of the sugars in binding to α1. Specific interactions with α1 of the modified digitoxose derivatives of DGlyN and DMe moieties are also indicated directly by the slower dissociation rates compared to digoxin (FIG. 9 and Table 4). Similarly increased selectivity of the more aliphatic derivatives in Table 6 such as DIB for the α2β3 complex over α1β1 may indicate a more specific interactions with βVal89. The present findings confirm and validate the concept that modification of the third digitoxose residues can increase selectivity for the α2 isoform.

In conclusion, the α2-selective digoxin derivatives described herein reduce intraocular pressure, and thus have the potential as novel drugs for control of IOP and prevention of glaucoma. When evaluated by the dose and especially duration of effects, the most α2-selective compounds DMe and DGlyN are significantly more effective than either the moderately α2-selective digoxin or non-selective digoxigenin. Furthermore when α2β3 selectivity is taken into account with the compounds such as DIB, superior effectiveness is observed. One important conclusion is that α2β3 indeed plays a major role in production of the aqueous humour, as could be predicted from its prominent expression in NPE cells.

The new perhydro-1,4-oxazepine derivatives described herein may also have a favorable safety profile, making them suitable as drug candidates. Local toxicity of α2β3-selective cardiac glycosides, namely swelling of the cornea and lens should be minimal because corneal endothelium express α1 and a minor amount of α3 but no α2, and lens epithelium express only α1. Also, systemic cardiotoxic effects should be minimal.

Lastly, perhydro-1,4-oxazepine derivatives of the more hydrophobic digitoxin may be even more effective than digoxin derivatives in reducing ocular hypertension, and/or as cardiotonic agents.

Example 5: Effects on Intra-Ocular Pressure in Rats

To evaluate whether the compounds of the present invention are able to control IOP in an animal model of chronic ocular hypertension, and to assess their local and systemic toxicity, ocular hypertension is being induced in rats, for example by impeding aqueous humour outflow using microbeads (24). Digoxin derivatives are added daily and IOP changes, signs of inflammation, corneal edema or lens clarity are followed. For systemic toxicity the concentration of the digoxin derivatives in the blood is measured by a radioimmunoassay.

Example 6: Experimental Section

Materials

*Escherichia* (*E.*) *coli* XL-1 blue strain was used for propagation and preparation of plasmid constructs. Yeast Lytic Enzyme from ICN Biomedicals Inc (cat. 152270) was used for transformation of *P. pastoris* protease deficient strain SMD1165 (his4, prb1). DDM (cat. D310) and C12E8 (25% w/w, cat no. 0330) were purchased from Anatrace. Synthetic SOPS (sodium salt)) was obtained from Avanti Polar Lipids, and stored as a chloroform solution. BD Talon metal affinity resin (cat. 635503) was obtained from Clontech. Cholesterol, ouabain (O3125, digoxin (D6003), 4-aminopyridine, (A78403) and IB-MECA (I146)) were obtained from Sigma. Methanol HPLC grade was purchased from Baker. All the organic solvents and amines were of highest purity analytical grade.

Preparation of hα1hβ1, hα1hβ2, hα1hβ3, hα2hβ1, hα2hβ2, hα2hβ3, hα3hβ1 Constructs Human β1, β2 and β3 were cloned into the pHIL-D2 expression vector containing the human α1 or α2. pHIL-D2 expression vectors containing porcine (p) α1, human (h) α1 or human α2 with Hisx10 tagged porcine β1 were previously generated (7, 9). Human β1 (Accession: P05026), human β2 (Accession: P14415) and human β3 (Accession: β54709) cDNAs in pSD5 vector were a gift from K. Geering Univ. Lausanne Switzerland. The open reading frames and flanking regions of hβ1, hβ2 and hβ3 (in pSD5) were amplified separately by polymerase chain reaction (PCR) using synthetic primers containing BglII and SalI cleavage sites. Each one of the amplified fragments were digested with BglII and SalI and ligated to BglII and SalI treated plasmid pHIL-D2-(pα1/His10pβ1) to generate pHIL-D2 (pα1/His10hβ1or2or3). hβ1, hβ2 and hβ3 containing fragments were excised from pHIL-D2-(pα1/His10hβ1or2or3) and subcloned into pHIL-D2-(hα1/His10pβ1) or pHIL-D2-(hα2/His10pβ1) to produce pHIL-D2-(hα1/His10hβ1or2or3) and pHIL-D2-(hα2/His10hβ1or2or3). The newly created plasmids were analyzed for correct integration and correct sequence of the insert by restriction enzymatic digestions and sequencing. DNA of each construct was prepared in large quantities in *E. coli* XL-1 Blue for *Pichia pastoris* transformation.

Yeast Transformation. Expression and Purification of Human Na,K-ATPase Isoforms

Methods for transformation, culture of *P. pastoris* clones, protein expression of Na,K-ATPase human isoforms (α1β1, α2β1, α3β1), membrane preparation, solubilization of membranes in DDM, and purification on BD-Talon beads have been described in detail (6-9, 11, 25). In initial experiments the three purified isoform complexes (0.3-0.5 mg/ml) were eluted from the BD-Talon beads in a solution containing Imidazole 170 mM, NaCl 100 mM; Tricine.HCl 20 mM pH 7.4; C12E8, 0.1 mg/ml; SOPS 0.07 mg/ml cholesterol 0.01 mg/ml, glycerol 25%. In later experiments the isoforms complexes were reconstituted with purified FXYD1 on the BD-Talon beads together as described in detail in (10, 11) prior to elution of α1β1FXYD1, α2β1FXYD1 and α3β1FXYD1 complexes. The proteins were stored at −80° C. Protein concentration was determined with BCA (B9643 Sigma).

Assay of Na,K-ATPase Activity of Purified Isoform Complexes

Inhibition of Na,K-ATPase activity of the detergent-soluble α1β1, α2β1, and α3β1 complexes by CG's was determined as described (6) using either the αβ or αβFXYD1 complexes. The presence or absence of FXYD1 does not affect inhibition of Na,K-ATPase activity by cardiac glycosides (6), but strongly stabilizes the complexes (9-11). The $K_{0.5}K$ was estimated by varying K concentration in a medium containing a fixed total K+choline chloride of 60 mM, and constant NaCl of 140 mM. Curves were fitted to the Hill function $v=V_{max}*[S]^n/([S]^n+K^n)$, where S is the K concentration, n is the Hill coefficient and $K^n$ is $K_{0.5}K$. For comparison of different curves the ratio v/Vmax for each curve was calculated and replotted. In experiments to assess inhibition of Na,K-ATPase activity by cardiac glycosides of the present invention, the percent inhibition VCG/V0 was calculated and Ki values were obtained by fitting the data to the function VCG/V0=Ki/([CG]+Ki)+c. Inhibition was estimated in 3-8 separate experiments and average Ki values ±SEM were calculated. Significance of differences between Kiα1 and Kiα2 was calculated by the unpaired Student's t-test (p values). The ratio of Kiα1/α2±SEM was calculated for each compound and p values were calculated by comparison with digoxin. P values <0.05 were considered significant.

Dissociation Rates of Cardiac Glycosides

Purified α2β1FXYD1 complexes (0.3-0.5 mg/ml) were incubated for 30 minutes at 37° C. in a medium containing ATP, 1 mM; NaCl 100 mM; MgCl$_2$, 4 mM Histidine.HCl 25 mM pH 7.4 without (Control) or with 1 μM of different cardiac glycosides. The enzyme solutions were then diluted 100-fold into a medium containing 100 mM NaCl, 5 mM KCl, 1 mM EDTA (Tris), 0.005 mg/ml C$_{12}$E8, 0.01 mg/ml SOPS, and 0.001 mg/ml cholesterol and incubated at 37° C. for different lengths of time. Aliquots were removed at different times and Na,K-ATPase activity was measured in triplicate over 0.5 minutes (digoxigenin) or 2 minutes (other cardiac glycosides) in the standard activity medium containing 200 μM ATP. The activity of test samples was divided by the activity of the control samples and the time-course for reversal of inhibition was analyzed by fitting the data to the function $v_t=v_\infty e^{-kt}+c$. Normalized curves for comparison of different experiments (e.g. as in FIG. 9) were obtained by subtracting the constant value c from each value of the activity and re-fitting the ratio $v_t/v_\infty=1-e^{-kt}$.

Synthesis of Perhydro-1,4-Oxazepine Derivatives of Digoxin

The syntheses of the different digoxin perhydro-1,4-oxazepine derivatives were performed in two steps: 1) oxidation of digoxin with sodium periodate to give an open-ring dialdehyde in the third sugar moiety and 2) reductive amination with a primary amine, in the presence of NaCNBH$_3$, closing a 7-membered ring to give the digoxin perhydro-1,4-oxazepine derivative. As an example, the synthesis of DGlyN is provided below. It is apparent to a person of skill in the art that the other compounds of the present invention may be prepared by the same or similar methods.

Oxidation of Digoxin with NaIO$_4$ (26)

In a 50 ml polypropylene test tube, a solution of NaIO$_4$ (400 mg, 1840 μmol) in H$_2$O (4 ml) was added under stirring at room temperature to a suspension of digoxin (400 mg, 512 μmol) in 95% EtOH (36 ml, not fully soluble) and the mixture that immediately dissolved was allowed to stand at room temperature for 1 hr. During that time a precipitate was formed. Precipitated NaIO$_3$ was removed, by centrifugation at 3,000×g for 15 min and filtration through a syringe filter (PTFE, 0.2 um, 25 mm). The solution was concentrated in an evaporator and extracted with 40 ml CHCl$_3$. The organic layer was washed with 2×8 ml water, dried over anhydrous Na$_2$SO$_4$, filtered and evaporated in an evaporator, and high vacuum overnight to give the dialdehyde, which is dissolved in 48 ml of absolute methanol to give a 10 mM solution of dialdehyde.

Reductive Amination with Glycinamide Hydrochloride

Glycinamide hydrochloride (28.2 mg, 256 μmoles, MW=110.54, Aldrich) was added to the digoxin dialdehyde (180 mg=240 μmoles) solution to give concentrations of 12 mM and 10 mM, respectively. The apparent pH was corrected to 5-6 with concentrated acetic acid in methanol, and the mixture was kept at room temperature for 5 min. The Schiff base that forms was reduced with NaCNBH$_3$, (59.6 mg, 480 μmoles, MW=123.95, 20 mM) with stirring. Progress of the reaction was monitored by TLC (SiO$_2$ with acetone/CHCl$_3$ (3:2). The mixture was left for 1.5 h, the creation of DGlyN and disappearance of digoxin dialdehyde was confirmed by mass spectrometry, and the methanol was evaporated by rotavap and high vacuum overnight. Since side reactions can occur, such as acid or base induced hydrolysis of dialdehyde to bis-digitoxoside, the final product was purified. The DGlyN reaction mixture was dissolved in a minimal amount (5.4 ml) of 50% methanol, filtered through a syringe filter 0.2 μm, PTFE, and used for purification by HPLC (FIG. 2B). HPLC purification was done on a Purospher STAR RP-18e semi-prep column, eluted with a gradient of 50-80% methanol in water in 15 column volumes at a flow rate of 4 ml/min. Other derivatives were purified using optimal gradients of methanol established in analytical HPLC runs (Chromolith RP-18e) prior to application to the semi-preparative column. The methanol was JT Baker HPLC gradient grade.

Additional compounds were prepared by a similar method. Their Mass Spectral data are presented in Table 1.

Digitoxin derivatives may be made by similar methods as described herein, using the digitoxin scaffold (X=H) instead of the digoxin scaffold (X=OH).

Measurement of Intraocular Pressure in Rabbits

Animals

New Zealand white rabbits (3-3.5 kg) about 1 year old, of either sex, were housed individually in separate cages in animal room conditions on a reversed, 12-hour dark/light cycle. For the experiments the animals were transferred to rabbit restrainers in a quiet and calm atmosphere (FIG. 1). No ocular abnormalities were detected prior or during the experiments. Animal care and treatment were subject to the approval of the institutional committee for animal experiments, Weizmann Institute IACUC permission (no 04270911-2).

Drug Preparation and Administration

Stock solutions of cardiac glycosides were dissolved in ethanol, and diluted in phosphate buffer (PBS) on each day of the experiment such that the final ethanol concentration did not exceed 1%.

Modeling

Digoxin (co-ordinates 3B0W) was introduced manually into the structure of pig kidney Na,K-ATPase bound with ouabain (4HYT) so that the steroid and lactone moieties of ouabain and digoxin superimposed as closely as possible, see ref. The structure file with bound digoxin was then submitted to the YASARA Energy Minimization Server. The structural figure was prepared with PyMOL.

Intraocular Pressure and Corneal Thickness Measurements

IOP (mm Hg) of rabbits was measured using a calibrated Pneumatonometer (Model 30, Reichert technologies, FIG. 1). A local anesthetic Oxybuprocaine HCl (0.4%, 25 μl) was applied to each cornea about a minute before IOP measurements. Two baseline IOP readings were taken before topical administration of the CG (or PBS as control) and after half an hour (Zero time). The readings of the two measurements were almost identical, suggesting that the CG's had no effect on the basal IOP. At zero time one drop of 4AP (40 mg/ml, 30 μl) or IB-MECA (1 μM, 30 μl) was administered to both eyes of each rabbit IOP measurements were made at different times as indicated in each experiment. In the experiments for which the IOP was elevated for several hours, 4AP was added every 1.5 hours or IB-MECA every 2 hours. The Pneumatonometer readings were accepted when the standard deviation of the value XmmHg was between 0.1-0.4 mmHg i.e X±0.1-0.4 mmHg, representing a possible error of 6-13% compared to the minimal 3 mm Hg increase and 1.6-6.7% compared to the maximal 6 mm Hg increase in IOP induced by 4AP or IB-MECA. Each experiment was repeated two or three times with similar results. In all cases the figures depict the average effect on IOP (i.e for four or six eyes) compared to control ±SEM. Where error bars are not seen in the figures, the errors are smaller than the symbols used. Significance of differences from the control was calculated by the unpaired Students t-test (p values), p values <0.05 were considered significant. Corneal thickness (μm) was measured using an ultrasonic pachymeter (Sonogage pachometer, Cleveland, USA), before and during the experiment with CG and 4AP treatments. The values represent averages of three independent measurements for each eye.

ABBREVIATIONS

IOP, intra-ocular pressure;
CG, cardiac glycoside;
4AP, 4-aminopyridine.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

REFERENCES

1. Simon K A & Bonting S L (1962) Possible usefulness of cardiac glycosides in treatment of glaucoma. *Arch Ophthalmol* 68:227-234.
2. Ferraiolo B L & Pace D G (1979) Digoxin-induced decrease in intraocular pressure in the cat. *Eur J Pharmacol* 55(1): 19-22.
3. Wetzel R K & Sweadner K J (2001) Immunocytochemical localization of NaK-ATPase isoforms in the rat and mouse ocular ciliary epithelium. *Invest Ophthalmol Vis Sci* 42(3):763-769.
4. Despa S, Lingrel J B, & Bers D M (2012) Na(+)/K)+)-ATPase alpha2-isoform preferentially modulates Cα2(+) transients and sarcoplasmic reticulum Cα2(+) release in cardiac myocytes. *Cardiovasc Res* 95(4):480-486.
5. Wasserstrom J A & Aistrup G L (2005) Digitalis: new actions for an old drug. *American journal of physiology. Heart and circulatory physiology* 289(5):H1781-1793.
6. Katz A, et al. (2010) Selectivity of digitalis glycosides for isoforms of human Na,K-ATPase. *J Biol Chem* 285(25): 19582-19592.
7. Cohen E, et al. (2005) Purification of Na+,K+-ATPase expressed in *Pichia pastoris* reveals an essential role of phospholipid-protein interactions. *J Biol Chem* 280(17): 16610-16618.
8. Haviv H, et al. (2007) Stabilization of Na(+),K(+)-ATPase purified from *Pichia pastoris* membranes by specific interactions with lipids. *Biochemistry* 46(44): 12855-12867.
9. Lifshitz Y, et al. (2007) Purification of the human alpha2 Isoform of Na,K-ATPase expressed in *Pichia pastoris*. Stabilization by lipids and FXYD1. *Biochemistry* 46(51): 14937-14950.

10. Mishra N K, et al. (2011) FXYD proteins stabilize Na,K-ATPase: amplification of specific phosphatidylserine-protein interactions. *J Biol Chem* 286(11):9699-9712.
11. Kapri-Pardes E, et al. (2011) Stabilization of the alpha2 isoform of Na,K-ATPase by mutations in a phospholipid binding pocket. *J Biol Chem* 286(50):42888-42899.
12. Ogawa H, Shinoda T, Cornelius F, & Toyoshima C (2009) Crystal structure of the sodium-potassium pump (Na+,K+-ATPase) with bound potassium and ouabain. *Proceedings of the National Academy of Sciences of the United States of America* 106(33): 13742-13747.
13. Yatime L, et al. (2011) Structural insights into the high affinity binding of cardiotonic steroids to the Na+,K+-ATPase. *J Struct Biol* 174(2):296-306.
14. Laursen M, Yatime L, Nissen P, & Fedosova N U (2013) Crystal structure of the high-affinity Na+,K+-ATPase-ouabain complex with Mg2+ bound in the cation binding site. *Proceedings of the National Academy of Sciences of the United States of America* 110(27): 10958-10963.
15. Adamczyk M, Grote J, & Mattingly P G (1995) Digoxin dialdehyde reductive aminations. Structure proof of the perhydro-1,4-oxazepine product. *Steroids* 60(11):753-758.
16. Socci R R, Chu E, Bayorh M A, & Chu T C (2003) 4-aminopyridine transiently increases intraocular pressure in rabbits. *Pharmacology* 69(2): 108-114.
17. Crambert G, et al. (2000) Transport and pharmacological properties of nine different human Na, K-ATPase isozymes. *J Biol Chem* 275(3): 1976-1986.
18. Carre D A, Mitchell C H, Peterson-Yantorno K, Coca-Prados M, & Civan M M (2000) Similarity of A(3)-adenosine and swelling-activated Cl(-) channels in non-pigmented ciliary epithelial cells. *Am J Physiol Cell Physiol* 279(2):C440-451.
19. Li A, Leung C T, Peterson-Yantorno K, Mitchell C H, & Civan M M (2010) Pathways for ATP release by bovine ciliary epithelial cells, the initial step in purinergic regulation of aqueous humor inflow. *Am J Physiol Cell Physiol* 299(6):C$_{1308}$-1317.
20. Yoda A & Yoda S (1974) Structure-activity relationships of cardiotonic steroids for the inhibition of sodium- and potassium-dependent adenosine triphosphatase. 3. Dissociation rate constants of various enzyme-cardiac glycoside complexes formed in the presence of sodium, magnesium, and adenosine triphosphate. *Molecular pharmacology* 10(3):494-500.
21. Hall C & Ruoho A (1980) Ouabain-binding-site photoaffinity probes that label both subunits of Na+,K+-ATPase. *Proceedings of the National Academy of Sciences of the United States of America* 77(8):4529-4533.
22. Ruoho A E & Hall C C (1980) The use of photolabels to probe the ouabain binding site of the (Na, K)-ATPase. *Annals of the New York Academy of Sciences* 346:90-103.
23. Katz A, et al. (2014) Digoxin Derivatives with Enhanced Selectivity for the alpha2 Isoform of Na,K-ATPase: EFFECTS ON INTRAOCULAR PRESSURE IN RABBITS. *J Biol Chem* 289(30):21153-21162.
24. Sappington R M, Carlson B J, Crish S D, & Calkins D J (2010) The microbead occlusion model: a paradigm for induced ocular hypertension in rats and mice. *Invest Ophthalmol Vis Sci* 51(1):207-216.
25. Strugatsky D, Goldshleger R, Bibi E, & Karlish S J (2003) Expression of Na,K-ATPase in *P. pastoris*: Fe2+-catalyzed cleavage of the recombinant enzyme. *Annals of the New York Academy of Sciences* 986:247-248.
26. Satoh D & Aoyama K (1970) Studies on Digitalis Glycosides. XXXI. Stepwise Degradation of Polydigitoxosides of Cardenolides. *Chem. Pharm. Bull.* 18(1):94-99.

What is claimed is:

1. A compound represented by the structure of general formula (I):

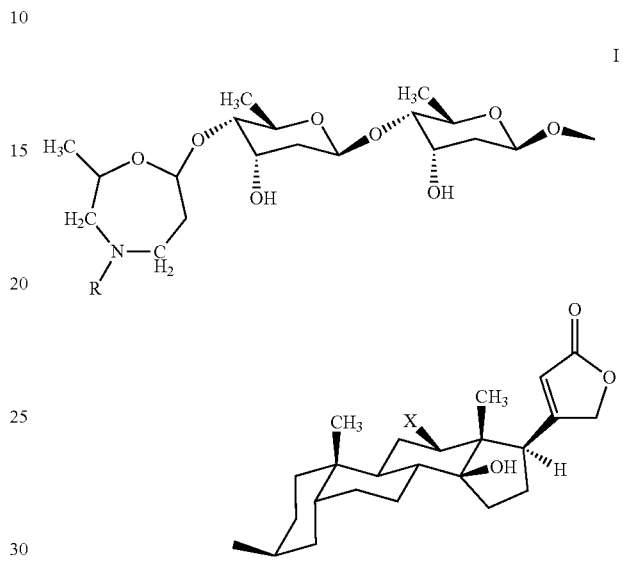

R is selected from the group consisting of —CH$_2$—C(=O)—NH$_2$ (compound 1), —CH$_3$ (compound 2), —(CH$_2$)$_2$—C(=O)—NH$_2$ (compound 3), —NHC(=O)—NH$_2$ (compound 4), —OH (compound 6), —CH(CH$_3$)CONH$_2$ (compound 8), —CH(CH$_2$OH)COOH (compound 9), —CH(CH$_2$OH)CONH$_2$ (compound 10), —CH$_2$CH$_3$ (compound 12), —(CH$_2$)$_2$CH$_3$ (compound 13), —CH$_2$CH(CH$_3$)$_2$ (compound 14), —CH$_2$CF$_3$ (compound 15), —CH$_2$C(=O)—NHOH (compound 17), —NHCSNH$_2$ (compound 18), —CH$_2$CH$_2$F (compound 19), and X is OH, including salts, hydrates, solvates, polymorphs, geometrical isomers, optical isomers, enantiomers, diastereomers, and mixtures thereof.

2. The compound of claim 1, being selective for α2 isoform of Na,K-ATPase over other isoforms of Na,K-ATPase.

3. The compound of claim 2, being selective for the α2β1, α2β2 and/or α2β3 isoform of Na,K-ATPase over the α1β1 isoform of Na,K-ATPase.

4. A pharmaceutical composition comprising the compound of claim 1, and a pharmaceutically acceptable carrier or excipient.

5. The composition of claim 4, being an ophthalmic composition suitable for topical application to the eye in the form of an eye-drop solution, an ointment, a suspension, a gel or a cream.

6. The composition of claim 4, for treating a condition selected from the group consisting of ocular hypertension, glaucoma and heart failure.

7. A method of treating a condition, comprising the step of administering to a subject in need of such a treatment an effective amount of the compound of claim 1 wherein said condition is selected from the group consisting of ocular hypertension, glaucoma and heart failure.

8. The method of claim 7, wherein the compound is selective for α2 isoform of Na,K-ATPase over other isoforms of Na,K-ATPase.

9. The method of claim 8, wherein the compound is selective for the α2β1, α2β2 and/or α2β3 isoform of Na,K-ATPase over the α1β1 isoform of Na,K-ATPase.

10. The method of claim 7, wherein the compound is administered in a pharmaceutical composition comprising said compound, and a pharmaceutically acceptable carrier or excipient.

* * * * *